United States Patent [19]

Ishiwa et al.

[11] Patent Number: 4,876,202

[45] Date of Patent: Oct. 24, 1989

[54] CHIMERIC PLASMIDS

[75] Inventors: Hiromi Ishiwa, Kodaira; Harue Shibahara, Nishitama; Masahiko Mutai, Higashiyamato; Nobuo Tsuchida, Yokohama, all of Japan

[73] Assignee: Kabushiki Kaisha Yakult Honsha, Tokyo, Japan

[21] Appl. No.: 125,396

[22] Filed: Nov. 18, 1987

Related U.S. Application Data

[63] Continuation-in-part of Ser. No. 574,180, Jan. 24, 1984, abandoned, and a continuation-in-part of Ser. No. 737,038, May 22, 1985, abandoned.

[30] Foreign Application Priority Data

| Jan. 24, 1983 | [JP] | Japan | 58-9740 |
| Jun. 8, 1983 | [JP] | Japan | 58-103196 |
| Aug. 31, 1983 | [JP] | Japan | 58-159345 |
| Jan. 10, 1984 | [JP] | Japan | 59-2361 |
| May 24, 1984 | [JP] | Japan | 59-105411 |

[51] Int. Cl.$^4$ .................. C12N 7/00; C12N 15/00; C07H 15/12
[52] U.S. Cl. ..................... 435/320; 435/170; 435/172.3; 435/252.31; 435/252.33; 536/27; 935/29; 935/56
[58] Field of Search ............. 435/68, 91, 170, 172.3, 435/252.1, 320, 848, 832; 536/27; 935/6, 8, 9, 10, 22, 23, 24, 27, 29, 59, 60, 61, 72, 73, 74, 56

[56] References Cited

U.S. PATENT DOCUMENTS 4,595,660  6/1986  Ostroff et al. ................. 435/172.3

OTHER PUBLICATIONS

Gray et al., 1981, *J. Bacterial*, 145:422–428.
Chang et al., 1978, *J. Bacteriol*, 134:1141–1155.
Clewell et al., 1975, *PNAS*, 72:1720–1724.
Maniatis et al., 1982, Molecular Cloning: A Laboratory Manual, Cold Spring Harbor Laboratory.
Burdett et al., "Multiple Tetracycline Resistance Determinants in Streptococcus", Microbiology, 1982.
Bal et al., Acta Microbiologica Polonica, 32 (34), 217–225, 1982.

*Primary Examiner*—Elizabeth C. Weimar
*Assistant Examiner*—Richard C. Peet
*Attorney, Agent, or Firm*—Wenderoth, Lind & Ponack

[57] ABSTRACT

A variety of chimeric plasmids each of which comprises (a) a tetracycline resistance gene (Tc) deriving from pAMα1, one of the plasmids retained by *Streptococcus faecalis*, (b) an ampicillin resistance gene (Amp) deriving from pACYC177, one of the vectors applicable to *Escherichia coli* and (c) either or both of origins, an origin (OripAMα1) deriving from the plasmid pAMα1 and an origin (Ori177) deriving from the vector pACYC177, the tetracycline resistance gene existing on each of which has the unique cleavage site for the restriction enzyme BalI on the entire DNA of the same plasmid and the ampicillin resistance gene existing on each of which has the unique cleavage sites for respective restriction enzymes BglI and PstI on the entire DNA on the same plasmid.

There is also provided a chimeric plasmid vector containing (a) a tetracycline resistance gene region (Tc) derived from the plasmid pAMα1 of *Streptococcus faecalis* DS5 (ATCC14508), (b) an ampicillin resistance gene region (Amp) derived from the vector pACYC177 of *E. coli*, (c) a first DNA replication origin (OripAMα1) derived from the plasmid pAMα1, (d) a second DNA replication origin (Ori177) derived from the vector pACYC177, and (e) a polylinker region having recognition and cleavage sites for the restriction enzymes EcoRI at one terminal and HindIII at the other terminal of the polylinker DNA sequence.

6 Claims, 14 Drawing Sheets

CHIMERIC PLASMIDS

This is a Continuation-in-part of Ser. No. 574,180, filed Jan. 24, 1984 abandoned, and Ser. No. 737,038, filed May 22, 1985, abandoned.

FIELD OF THE INVENTION

The present invention relates to a variety of chimeric plasmids which are useful as cloning vectors functioning at least for *Escherichia coli* and/or *Bacillus subtilis* and which are synthesized from a plasmid retained by *Streptococcus faecalis*, one of the gram-positive bacteria, and a vector taken out of *E. coli*, one of the gram-negative bacteria. More specifically, the present invention relates to a variety of chimeric plasmids each of which comprises (a) a tetracycline resistance gene (Tc) deriving from pAMα1, one of the plasmids retained by *S. faecalis*, (b) an ampicillin resistance gene (Amp) deriving from pACYC177, one of the vectors applicable to *E. coli*, and (c) either or both of the areas at which replication originates (hereinafter referred to as an origin) (OripAMα1) deriving from the aforementioned plasmid pAMα1 and the origin (Ori177) deriving from the aforementioned plasmid pACYC177, wherein the aforementioned tetracycline resistance gene contains the only site at which the chimeric plasmid is specifically cleaved by the restriction enzyme BalI and the aforementioned ampicillin resistance gene contains the only site at which the chimeric plasmid is specifically cleaved by the restriction enzymes BglI and PstI.

The present invention also relates to a specific group of novel chimeric plasmids vector which are also useful as a cloning vector for *Escherichia coli* or *Bacillus subtilis*. These chimeric plasmids contain (a) tetracycline resistance gene region (Tc) derived from the plasmid pAMα1 of *Streptococcus faecalis* DS5 (ATCC14508), (b) and ampicillin resistance gene region (Amp) derived from the vector pACYC177 of *E. coli*, (c) at first DNA replication origin (OripAMα1) derived from the plasmid pAMα1, (d) a second DNA replication origin (Ori177) derived from the vector pACYC177, and (e) a polylinker region having recognition and cleavage sites for the restriction enzymes EcoRI at one terminal and HindIII at the other terminal of the polylinker DNA sequence.

BACKGROUND OF THE INVENTION

Insofar as an in vitro gene manipulation technology is concerned, it is required that a vector which is accepted by a host be available to allow a foreign DNA to migrate in a cell of the host and to allow the foreign DNA to express the genetic information thereof in the cell of the host. The behavior of a vector is clear, to a considerable extent, for the host-vector system in which *Escherichia coli* is employed, because efforts have been concentrated thereon so far. At present, however, many efforts are being used for development of host-vector systems which employ various microorganisms other than *E. coli*, such as *Bacillus subtilis* which is one of the microorganisms useful from the industrial viewpoint, Actinomycetes which are microorganisms capable of producing antibiotics, and yeast which is widely employed for brewing.

The fundamental requirements for a vector are that the vector has a gene arrangement which is necessary for replication and that the vector has a recognition and cleavage site for a restriction enzyme at which a foreign DNA is inserted. From the practical viewpoint, however, various additional items tabulated below are required for a vector:

1. Each of the specific restriction enzymes which can be employed for a specific gene manipulation has a recognition and cleavage site which is convenient in later steps in the specific gene manipulation process.
2. The vector has a high efficiency in expression of genetic information.
3. The vector has a marker gene which is necessary for detection of a transformant.
4. The vector is readily accepted by a specific host, and the vector has a convenient host range.
5. The vector is stable in the specific host without incurring disturbance.
6. The vector allows a biological confinement which is aimed at reduction of possibilities of any potential biological hazards.

This is the reason why only a few successful cases have been reported for the practically useful vectors even within the category of the host-vector systems employing *E. coli* or *B. subtilis*.

In view of the aforementioned facts, we have been using our best efforts for acquisition of plasmid vectors useful for the ultimate purposes of developing host-vector systems which employ *E. coli*, the biological properties of which are well known and *B. subtilis*, which is useful for the industrial purpose of producing amylase et al. As a result, applicants were successful in development of a variety of chimeric plasmids which are synthesized from a plasmid retained by *Streptococcus faecalis*, pAMα1, and a vector applicable to *E. coli*, pACYC177, and which are excellent vectors for gene manipulation employing *E. coli* or *B. subtilis*.

Applicants have further put forth efforts to develop more useful plasmid vectors. These continued efforts have now resulted in development of excellent chimeric shuttle vectors which not only have beneficial microbial properties comparable to those of known plasmid vectors but also permit of the use of various restriction enzymes. The present invention is particularly concerned with these novel, useful vector.

SUMMARY OF THE INVENTION

A variety of chimeric plasmids in accordance with the present invention are those which are produced by cleaving pAMα1, a plasmid retained by Streptococcus faecalis DS5 (ATTCC14508), and pACYC177, a vector applicable to *Escherichia coli* and by lighting the cleaved DNA fragments of the foregoing plasmid and vector to include a tetracycline resistance gene (Tc) deriving from the aforementioned pAMα1, an ampicillin resistance gene (Amp) deriving from the aforementioned pACYC177 and either or both of the origin (OripAMα1) deriving from the aforementioned pAMα1 and the origin (Ori177) deriving from the aforementioned pACYC177.

The chimeric plasmids included in the aforementioned genus category are classified, following the difference in the dimension of the reduced molecular weight, into 10 species including pHY780, pHY600, pHY460, pHY385, pHY360, pHY340, pHY330, pHY310, pHY285 and pHY225.

Since each of the aforementioned chimeric plasmids has a tetracycline resistance gene and an ampicillin resistance gene in its DNA, they have the capability of providing a host with resistance against both tetracycline and ampicillin during the transformation process applied to E. coli. They also have the capability of providing a host with resistance against tetracycline during the transformation process applied to Bacillus subtilis. This generic nature is allowed to function as a marker for detection and selection of a transformant or a host which retains a chimeric plasmid in which a desired foreign DNA is to be inserted. Further, since the tetracycline resistance gene of any of the chimeric plasmids in accordance with the present invention contains the unique site at which the chimeric plasmid is recognized and cleaved by restriction enzyme BalI, and also since the ampicillin resistance gene of any of the same chimeric plasmids contains the respective unique sites at which the chimeric plasmid is recognized and cleaved by respective restriction enzymes BglI and PstI, no more fragments than are required are produced from any of the chimeric plasmids in accordance with the present invention, provided the restriction enzymes employed for the cleavage are limited to the aforementioned ones.

Accordingly, a foreign DNA can be inserted in one of the aforementioned unique sites. The tetracycline resistance gene is cleaved by the restriction enzyme BalI to form a pair of flush ends at the center of the 6-nucleotide sequence of the DNA. Thus, it is possible, without utilizing T4 DNA polymerase or S1 nuclease, to ligate the aforementioned flush ends with any of the foreign DNA fragments each of which has a pair of flush ends. No limitations are imposed on the method for production of the foreign DNA-s having flush ends. In other words, not only the aforementioned restriction enzymes but also any other restriction enzymes which produce flush ends can be employed for preparation of the foreign DNA-s. Further, it is possible to produce a ligated DNA employing foreign DNA fragments having artificially produced flush ends.

Out of the chimeric plasmids in accordance with the present invention, pHY460, pHY385, pHY360, and pHY340 and pHY310 are qualified to function as shuttle vectors which are applicable both to E. coli and B. subtilis. This is because the aforementioned two independent origins, namely, OripAMα1, the origin deriving from the plasmid, pAMα1, and Ori177, the origin deriving from the vector, pACYC177, both of which are contained in any of the chimeric plasmids in accordance with the present invention, are correctly interpreted and allowed to enjoy stable replications not only in E. coli but also in B. subtilis, resultantly being allowed to express the tetracycline resistance gene at least in each of E. coli and B. subtilis.

The DNA cloning system in which the progress in research and development has most extensively been achieved is the vector system (EK system) employing E. coli, one of the gram-negative bacteria and its vectors. In accordance with this system, genes deriving from the gram-negative bacteria and some specific genes deriving from the gram-positive bacteria are allowed to be expressed.

In contrast, many problems still remain unsolved for the system employing the gram-positive bacteria. This is the reason why a considerable amount of attention is paid to this subject. Particularly, albeit B. subtilis is a group of useful microorganisms which have a number of practical advantages; they have biological properties which are entirely different from those of E. coli. Thus, the study of the genetic information of B. subtilis and the development of a cloning system employing the same bacteria have become matters of great interest.

Under such conditions, the industry is eager to develop a host-vector system employing B. subtilis. Therefore, our success in development of a variety of shuttle vectors which are applicable both the E. coli, a typical gram-negative bacteria, and B. subtilis, a typical gram-positive bacteria, is of considerable significance, because it is recognized as a milestone towards reaching a DNA cloning system employing gram-positive bacteria. Accordingly, it is clear that the chimeric plasmids in accordance with the present invention are useful from the industrial viewpoint.

In addition, since possibilities are assumed for utilization of some of the chimeric plasmids in accordance with the present invention for the purposes of gene analysis and molecular breeding of the other gram-positive bacteria, e.g. those belonging to Lactobacillus, Bifidobacterium and the like, chimeric plasmids in accordance with the present invention are promising from the viewpoint of industrial application thereof.

BRIEF DESCRIPTION OF THE DRAWINGS

The present invention, together with its various features and advantages, can be readily understood from the following more detailed description presented in conjunction with the following drawings, in which.

Figure 1:
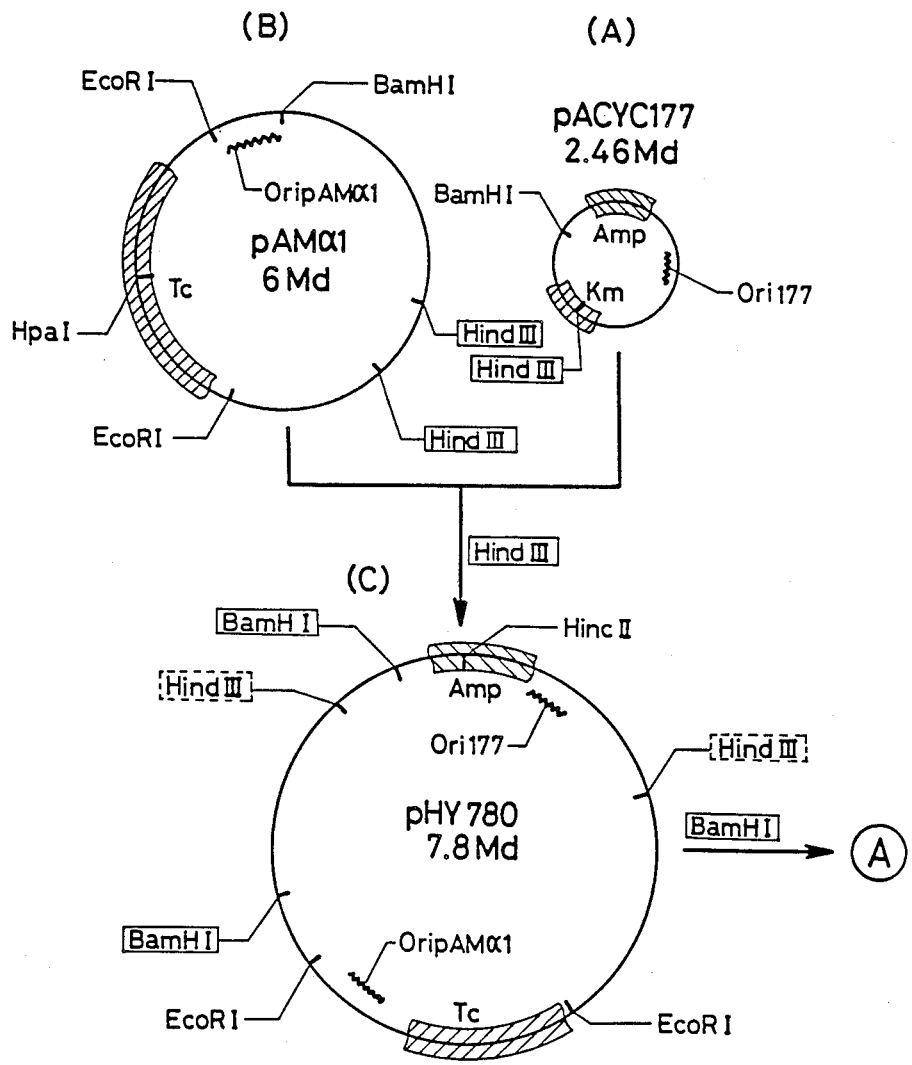
FIG. 1(A) is a process chart showing the synthesis process of one of the chimeric plasmids in accordance with the present invention, pHY780.
FIG. 1(B) is a process chart showing the synthesis process of some of the chimeric plasmids in accordance with the present invention, pHY600, pHY460, pHY360 and pHY385.
Figure 1B:
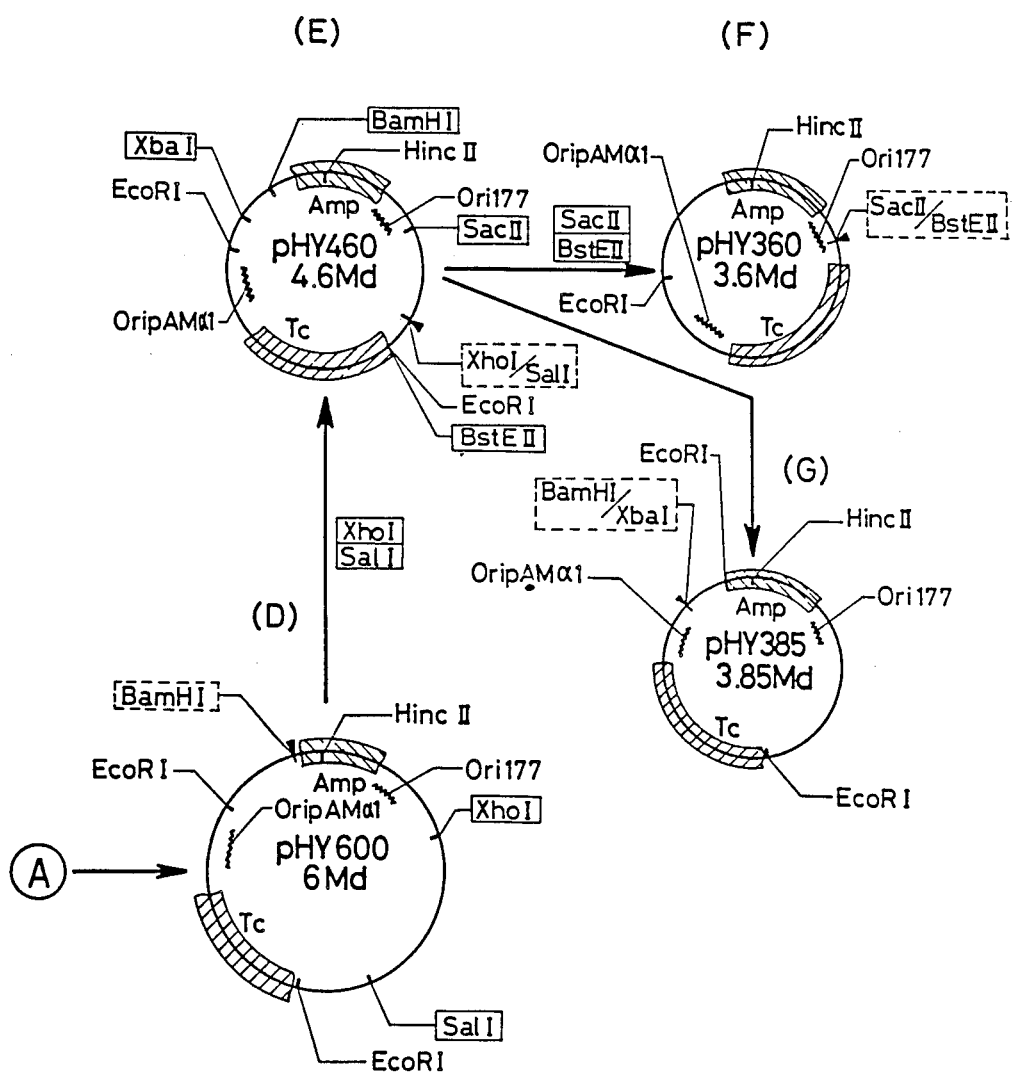
Figure 2:
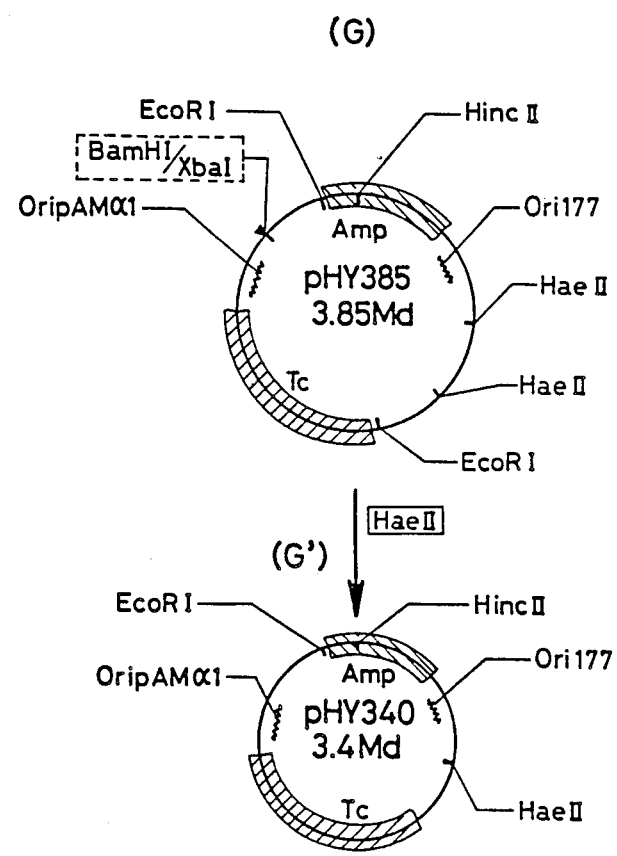
FIG. 2 is a process chart showing the synthesis process of one of the chimeric plasmids in accordance with the present invention, pHY340.
Figure 3:
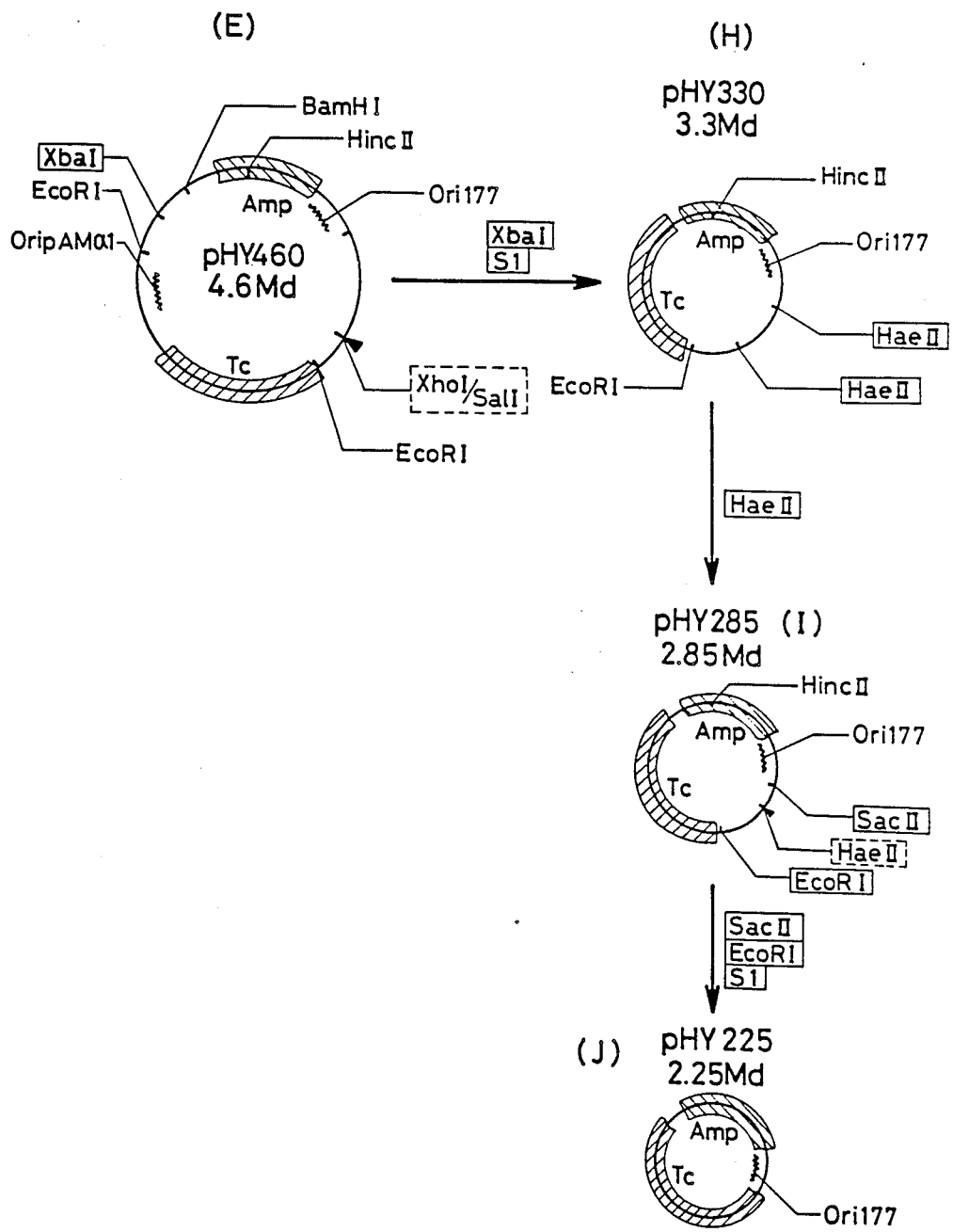
FIG. 3 is a process chart showing the synthesis process of some of the chimeric plasmids in accordance with the present invention, pHY330, pHY285 and pHY225.
Figure 4:
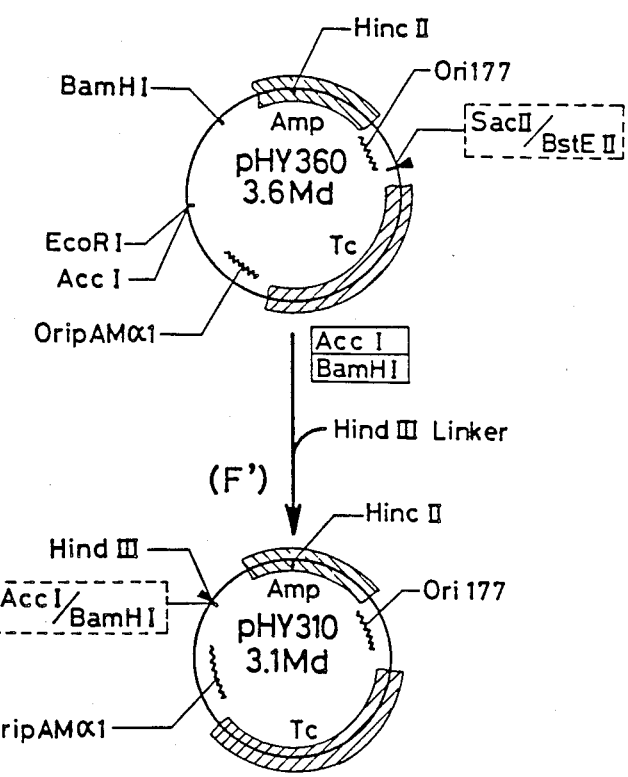
FIG. 4 is a process chart showing the synthesis process of one of the chimeric plasmids in accordance with the present invention pHY310.

In connection with above FIGS. 1 to 3, it should be noted that FIGS. 1 through 3 show the synthesis progress of the chimeric plasmids in accordance with the present invention, which starts at the vector pACY177 (shown as (A) in FIG. 1(A)) and the plasmid pAMα1 (shown as (B) in FIG. 1(A)) to arrive at chimeric plasmids pHY385 (shown as (G) in FIG. 1(B)), pHY360 (shown as (F) in FIG. 1(B)), pHY340 (shown as (G') in FIG. 2), pHY330 (shown as (H) in FIG. 3), pHY310 (shown as (F') in FIG. 4), pHY285 (shown as (I) in FIG. 3) and pHY225 (shown as (J) in FIG. 3), passing through the chimeric plasmids pHY780 (shown as (C) in FIG. 1(A)), pHY600 (shown as (D) in FIG. 1(B)) and pHY460 (shown as (E) in FIG. 1(B)).

The character of each of the chimeric plasmids in accordance with the present invention will be described below:

DETAILED DESCRIPTION

Chimeric plasmid pHY780

(1) The chimeric plasmid pHY780 is a circular deoxyribonucleic acid (DNA) of which the molecular weight is approximately 7.8 Md.

(2) pHY780 is a chimeric plasmid which is constructed by ligating a larger fragment of a linear DNA which is produced by digesting a plasmid pAMα1 containing a tetracycline resistance gene (Tc) with a restriction enzyme HindIII and a fragment of a linear DNA which is produced by digesting a plasmid vector pACYC177 containing an ampicillin resistance gene (Amp) and a kanamycin resistance gene (Km) with the same enzyme HindIII.

The plasmid pAMα1 and the vector pACYC177 both of which are employed as the starting materials for the aforementioned synthesis process are publicly known (pAMα1: Proc. Natl. Acad. Sci. U.S.A., 72, 1720–1724 (1975), pACYC177: J. Bacteriol., 134, 1141–1156(1978)).

(3) pHY780 includes an ampicillin resistance gene (Amp) which contains the respective unique sites at which the chimeric plasmid is recognized and cleaved by respective restriction enzymes BglI and PstI and a tetracycline resistance gene (Tc) which contains the unique site at which the chimeric plasmid is recognized and cleaved by the restriction enzyme BalI. Accordingly, these recognition and cleavage sites can be utilized as the insertional inactivation site at which a foreign DNA is inserted.

The following table lists the quantity of recognition and cleavage sites at which pHY780 is cleaved by various restriction enzymes:

| Restriction Enzyme | Quantity of Recognition and Cleavage Sites |
|---|---|
| BalI | 1 |
| BamHI | 2 |
| BanI | 1 or more |
| BglI | 1 |
| EcoRI | 2 |
| EcoRV | 1 or more |
| HaeII | 4 |
| HindIII | 3 |
| HpaI | 2 |
| KpnI | 2 |
| PstI | 1 |
| PvuI | 2 |
| SacII | 1 |
| SalI | 1 |
| XbaI | 1 |
| XhoI | 1 |

The tabulated quantity of recognition and cleavage sites were determined by counting the quantity of the recognizable bands which were generated on an electrophothesis agarose gel by the DNA fragments produced by digestion of pHY780 under the excess quantity of various restriction enzymes.

(4) pHY780 replicates in *E. coli*, gram-negative bacteria. In addition, pHY780 gives a host the resistance deriving from the ampicillin resistance gene (Amp) and the tetracycline resistance gene (Tc), both of which exist in the specific regions on the DNA sequence of pHY780. This resistance can be utilized as a selection marker for a transformant.

Chimeric plasmid pHY600

(1) The chimeric plasmid pHY600 is a circular DNA of which the molecular weight is approximately 6.0 Md.

(2) pHY600 is a chimeric plasmid which is constructed by the following process:

(i) Restriction enzyme BamHI is employed to cleave the thereof by depriving pHY780 of a DNA fragment whose molecular weight is approximately 1.8 Md.

(ii) T4 ligase is employed to ligate the both cohesive ends of the shortened DNA fragment to produce a circular DNA.

(iii) As is in the case of pHY780, the pHY600 includes an ampicillin resistance gene (amp) which contains the only site at which the chimeric plasmid is recognized and cleaved by respective restriction enzymes BglI and PstI and a tetracycline resistance gene (Tc) which contains the respective unique sites at which the chimeric plasmid is recognized and cleaved by the restriction enzyme BalI. Accordingly, these recognition and cleavage sites can be utilized as the insertional inactivation site at which a foreign DNA in inserted.

The following table lists the quantity of recognition and cleavage sites at which pHY600 is cleaved by various restriction enzymes:

| Restriction Enzyme | Quantity of Recognition and Cleavage Sites |
|---|---|
| BalI | 1 |
| BamHI | 1 |
| BanI | 1 or more |
| BglI | 1 |
| EcoRI | 2 |
| EcoRV | 1 or more |
| HaeII | 2 |
| HindIII | 1 |
| HpaI | 2 |
| PstI | 1 |
| PvuI | 2 |
| SacII | 1 |
| SalI | 1 |
| XbaI | 1 |
| XhoI | 1 |

(4) As is in the case of pHY780, pHY600 replicates in E. coli, gram-negative bacteria. In addition, pHY600 gives a host the resistance deriving from the tetracycline resistance gene (Tc) and the ampicillin resistance gene (Amp). Accordingly, pHY600 is allowed to function as a cloning vector for at least E. coli.

Chimeric plasmid pHY460

(1) The chimeric plasmid pHY460 is a circular DNA of which the molecular weight is approximately 4.6 Md.

(2) pHY460 is a chimeric plasmid which is constructed by the following process:

(i) Restriction enzymes XhoI and SalI are employed to cleave the aforementioned pHY600 to shorten the DNA dimension thereof by depriving pHY600 of a DNA fragment whose molecular weight is approximately 1.4 Md.

(ii) T4 ligase is employed to ligate the both cohesive ends of the shortened DNA fragment to produce a circular DNA.

(3) pHY460 includes an ampicillin resistance gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY460 is cleaved by various restriction enzymes:

| Restriction Enzyme | Quantity of Recognition and Cleavage Sites |
|---|---|
| BalI | 1 |
| BamHI | 1 |
| BanI | 1 |
| BglI | 1 |
| BstEII | 1 |
| EcoRI | 2 |
| EcoRV | 1 |
| HaeII | 2 |
| HpaI | 1 |
| PstI | 1 |
| PvuI | 1 |
| SacII | 1 |
| XbaI | 1 |

(4) pHY460 replicates not only in E. coli, gram-negative bacteria, but also in B. subtilis, gram-positive bacteria. In addition, pHY460 gives a host the resistance deriving from the tetracycline resistance gene. Accordingly, pHY460 is allowed to function as a cloning vector (a shuttle vector) at least both for E. coli and for B. subtilis.

Chimeric plasmid pHY360

(1) The chimeric plasmid pHY360 is a circular DNA of which the molecular weight is approximately 3.6 Md.

(2) pHY360 is a chimeric plasmid which is constructed by the following process:

(i) Restriction enzymes SacII and BstEII are employed to cleave the aforementioned pHY460.

(ii) The larger DNA fragment is digested with S1 nuclease to make the both ends thereof flush.

(iii) T4 ligase is employed to ligate the both flush ends of the DNA fragment to produce a circular DNA.

(3) pHY360 includes an ampicillin resistance gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY360 is cleaved by various restriction enzymes:

| Restriction Enzyme | Quantity of Recognition and Cleavage Sites |
| --- | --- |
| BalI | 1 |
| BamHI | 1 |
| BanI | 1 |
| BglI | 1 |
| EcoRI | 1 |
| EcoRV | 1 |
| HpaI | 1 |
| PstI | 1 |
| PvuI | 1 |
| XbaI | 1 |

(4) As is in the case of pHY460, pHY360 replicates not only in E. coli, gram-negative bacteria but also in B. subtilis, gram-positive bacteria. In addition, pHY360 gives a host the resistance against tetracycline. Accordingly, pHY360 is allowed to function as a cloning vector (a shuttle vector) at least both for E. coli and for B. subtilis.

A successive cultivation test was conducted for 50 generations to determine the stability of pHY360 in B. subtilis. The results of the test showed that approximately 10% of the transformants were resistant to tetracycline after the 50-generation successive cultivation test.

Chimeric plasmid pHY310

(1) The chimeric plasmid pHY310 is a circular DNA of which the molecular weight is approximately 3.1 Md.

(2) pHY310 is a chimeric plasmid which is constructed by the following process:

(i) Restriction enzymes AccI and BamHI are employed to cleave the aforementioned pHY360.

(ii) The both cohesive ends of the cleaved DNA fragment are converted into a pair of flush ends by treating them with T4 DNA polymerase and 4 kinds of deozyribonucleoside triphosphate.

(iii) T4 ligase is employed to ligate each of the flush ends of the larger DNA fragment (produced by digestion of pHY360) and each of the flush ends of a HindIII linker (dpCAAGCTTG), which bridges the both ends of the same DNA fragment to produce a circular DNA.

(3) pHY310 includes an ampicillin resistance gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

In addition, since on the sequence of the bridging HindIII linker, there exists the unique site at which the chimeric plasmid is recognized and cleaved by the restriction enzyme HindIII, this recognition and cleavage site is also counted for the position at which a foreign DNA is inserted.

The following table lists the quantity of recognition and cleavage sites at which pHY310 is cleaved by various restriction enzymes:

| Restriction Enzyme | Quantity of Recognition and Cleavage Sites |
| --- | --- |
| BalI | 1 |
| BanI | 1 |
| BglI | 1 |
| EcoRI | 1 |
| HincII | 3 |
| HindIII | 1 |
| HpaI | 1 |
| PstI | 1 |
| PvuI | 1 |

(4) As in the case of pHY360, pHY310 replicates not only in E. coli, gram-negative bacteria, but also in B. subtilis, gram-positive bacteria. In addition, pHY310 gives a hose the resistance against tetracycline. Accordingly, pHY310 is allowed to function as a cloning vector (a shuttle vector) at least both for E. coli and for B. subtilis.

Chimeric plasmid pHY385

(1) The chimeric plasmid pHY385 is a circular DNA of which the molecular weight is approximately 3.85 Md.

(2) pH385 is a chimeric plasmid which is obtained by the following process:

(i) A microorganism belonging to B. subtilis is transformed by the aforementioned pHY460.

(ii) The transformants are cultivated for 50 successive generations to shorten the DNA dimension thereof by depriving pHY460 of a DNA fragment whose molecular weight is approximately 0.75 Md.

(3) pHY385 includes an ampicillin resistance gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY385 is cleaved by various restriction enzymes:

| Restriction Enzyme | Quantity of Recognition and Cleavage Sites |
| --- | --- |
| BalI | 1 |
| BanI | 1 |
| BglI | 1 |

| Restriction Enzyme | Quantity of Recognition and Cleavage Sites |
|---|---|
| BstEII | 1 |
| EcoRI | 2 |
| EcoRV | 1 |
| HaeII | 2 |
| HpaI | 1 |
| PstI | 1 |
| PvuI | 1 |
| SacII | 1 |

(4) As is in the case of pHY460, pHY385 replicates not only in *E. coli*, gram-negative bacteria, but also in *B. subtilis*, gram-positive bacteria. In addition, pHY385 gives a host the resistance against tetracycline. Accordingly, pHY385 is allowed to function as a cloning vector (a shuttle vector) at least both for *E. coli* and for *B. subtilis*.

Chimeric plasmid pHY340

(1) The chimeric plasmid pHY340 is a circular DNA of which the molecular weight is approximately 3.4 Md.

(2) pHY340 is a chimeric plasmid constructed by the following process:

(i) Restriction enzyme HaeII is employed to cleave the aforementioned pHY385 to shorten the DNA dimension thereof by depriving pHY385 of a DNA fragment whose molecular weight is approximately 0.45 Md.

(ii) T4 ligase is employed to ligate the both cohesive ends of the shortened DNA fragment to produce a circular DNA.

(3) pHY340 includes an ampicillin gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY340 is cleaved by various restriction enzymes:

| Restriction Enzyme | Quantity of Recognition and Cleavage Sites |
|---|---|
| BalI | 1 |
| BanI | 1 |
| BglI | 1 |
| BstEII | 1 |
| EcoRI | 2 |
| EcoRV | 1 |
| HaeII | 1 |
| HpaI | 1 |
| PstI | 1 |
| PvuI | 1 |
| SacII | 1 |

(4) pHY340 replicates not only in *E. coli*, gram-negative bacteria, but also in *B. subtilis*, gram-positive bacteria. In addition, pHY340 gives a host the resistance against tetracycline. Accordingly, pHY340 is allowed to function as a cloning vector (a shuttle vector) at least both for *E. coli* and for *B. subtilis*.

Chimeric plasmid pHY330

(1) The chimeric plasmid pHY330 is a circular DNA of which the molecular weight is approximately 3.3 Md.

(2) pHY330 is a chimeric plasmid produced by the following process:

(i) pHY460 is cleaved by the restriction enzyme XbaI to produce a linear DNA fragment, before the fragment is subjected to digestion with S1 nuclease to be shortened in random length and to have a pair of flush ends.

(iii) T4 ligase is employed to ligate the both flush ends of the shortened DNA fragment to produce a circular DNA.

(3) pHY330 includes an ampicillin resistance gene (Amp) which contains the respective unique sites at which the chimeric plasmid is recognized and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY330 is cleaved by various restriction enzymes:

| Restriction Enzyme | Quantity of Recognition and Cleavage Sites |
|---|---|
| BalI | 1 |
| BanI | 1 |
| BglI | 1 |
| BstEII | 1 |
| EcoRI | 1 |
| EcoRV | 1 |
| HaeII | 2 |
| HpaI | 1 |
| PstI | 1 |
| PvuI | 1 |

| Restriction Enzyme | Quantity of Recognition and Cleavage Sites |
| --- | --- |
| SacII | 1 |

(4) As is in the case of pHY780, pHY330 replicates in *E. coli*, gram-negative bacteria. In addition, pHY330 gives a host the resistance against tetracycline and ampicillin. Accordingly, pHY330 is allowed to function as a cloning vector at least for *E. coli*.

This chimeric plasmid pHY330, as well as the chimeric plasmids pHY285 and pHY225 which will be described later, is lack of the origin (OripAMα1) which derives from the plasmid pAMα1 but retains the origin (Ori177) which derives from the vector pACYC177. Thus, pHY330 does not replicate in gram-positive bacteria.

Chimeric plasmid pHY285

(1) The chimeric plasmid pHY285 is a circular DNA of which the molecular weight is approximately 2.85 Md.

(2) pHY285 is a chimeric plasmid constructed by the following process:

(i) pHY330 is cleaved by the restriction enzyme HaeII to shorten the DNA dimension thereof by depriving pHY285 of a DNA fragment whose molecular weight is approximately 0.45 Md.

(ii) T4 ligase is employed to ligate the both cohesive ends of the shortened DNA fragment to produce a circular DNA.

(3) pHY285 includes an ampicillin resistance gene (Amp) which contains the respective unique sites at which the chimeric plasmid is recognized and cleaved by and cleaved by respective restriction enzymes BglI, PstI, BanI and PvuI and a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY285 is cleaved by various restriction enzymes:

| Restriction Enzymes | Quantity of Recognition and Cleavage Sites |
| --- | --- |
| AccI | 1 |
| BalI | 1 |
| BanI | 1 |
| BglI | 1 |
| BstEII | 1 |
| EcoRI | 1 |
| EcoRII | 4 |
| EcoRV | 1 |
| HaeII | 1 |
| HpaI | 1 |
| PstI | 1 |
| PvuI | 1 |
| SacII | 1 |

(4) As in the case of pHY330, pHY285 replicates in *E. coli*, gram-negative bacteria. In addition, pHY285 gives a host the resistance against tetracycline and ampicillin. Accordingly, pHY285 is allowed to function as a cloning vector at least for *E. coli*.

Chimeric plasmid pHY225

(1) The chimeric plasmid pHY225 is a circular DNA of which the molecular weight is approximately 2.25 Md.

(2) pHY225 is a chimeric plasmid constructed by the following process:

(i) Restriction enzymes SacII and EcoRI are employed to cleave the aforementioned pHY285 to shorten the DNA dimension thereof by depriving pHY285 of a DNA fragment whose molecular weight is approximately 0.6 Md.

(ii) The shortened DNA fragment is digested with S1 nuclease to make the both ends thereof flush.

(iii) T4 ligase is employed to ligate the both flush ends of the DNA fragment to produce a circular DNA.

(3) pHY225 includes an ampicillin resistance gene (Amp) which contains the respective unique sites at which the chimeric plasmid is recognized and cleaved by respective restriction enzymes BglI, PstI, BanI and PvuI a tetracycline resistance gene (Tc) which contains the respective unique sites at which the chimeric plasmid is recognized and cleaved by respective restriction enzymes BalI, EcoRV and HpaI. Accordingly, these recognition and cleavage sites can be utilized as the insertional inactivation site at which a foreign DNA is inserted.

The following table lists the quantity of recognition and cleavage sites at which pHY225 is cleaved by various restriction enzymes:

| Restriction Enzymes | Quantity of Recognition and Cleavage Sites |
| --- | --- |
| BalI | 1 |
| BanI | 1 |
| BglI | 1 |
| BstEII | 1 |
| EcoRII | 2 |
| EcoRV | 1 |
| HincII | 3 |
| HpaI | 1 |
| PstI | 1 |
| PvuI | 1 |

(4) As is in the case of pHY285, pHY225 replicates in *E. coli*, gram-negative bacteria. In addition, pHY225 gives a host the resistance against tetracycline and ampicillin. Accordingly, pHY225 is allowed to function as a cloning vector at least for *E. coli*.

Each of the aforementioned chimeric plasmids in accordance with the present invention, namely, pHY780, pHY600, pHY460, pHY385, pHY360, pHY330, pHY310, pHY285 and pHY225, fully satisfies the requirements for a vector useful for closing an arbitrary gene at least in the DNA recombination technology employing *E. coli* as a host. In other words, they have a function to convey an arbitrary gene picked up out of other microorganisms and the like, into a host to retain and express the same gene therein. As a result, each of the chimeric plasmids in accordance with the present invention is allowed to be utilized as a vector for a type of DNA recombination technology, wherein a vector is caused to pick up the specific gene which has the capacity to be involved with bio-synthesis of a useful material or with the adjustment of bio-synthesis of a useful material out of a microorganism or the like, to convey the gene toward a host including at least *E. coli*, and to retain the gene in the microorganism, thereby the host is allowed to clone the specific gene to express its genetic information therein. Further, each of the chimeric plasmids in accordance with the present invention can be utilized for strengthening the bio-synthesis system by means of the function of amplifying the genetic information specified by a specific gene, thereby enabling the productivity to be improved for the aforementioned useful material. Particularly, pHY460, pHY385, pHY360, pHY340 and pHY310 fully satisfy the requirements for a shuttle vector which is applicable at least both to *E. coli* and *B. subtilis* during the process of the aforementioned DNA recombination technology. In other words, these plasmids have, in addition to the function described above, a function to convey a gene from one host back to another host. As a result, each of these chimeric plasmids is allowed to be utilized as a shuttle vector for a type of DNA recombination technology in a much more convenient manner than was described above.

Further, pHY460, pHY385, pHY360, pHY340 and pHY310 can be utilized for expressing various genes deriving from some other microorganisms or the like, in gram-positive bacteria of which a typical example is *B. subtilis*. Therefore, these chimeric plasmids can provide means effective for gene analysis and molecular breeding of gram-positive bacteria.

Further, in accordance with the present invention, there is provided a chimeric plasmid vector containing (a) a tetracycline resistance gene region (Tc) derived from the plasmid pAMα1 of *Streptococcus faecalis* DS5 (ATCC14508), (b) an ampicillin resistance gene region (Amp) derived from the vector pACYC177 of *E. coli*, (c) a first DNA replication origin (OripAMα1) derived from the plasmid pAMα1, (d) a second DNA replication origin (Ori177) derived from the vector pACYC177, and (e) a polylinker region having recognition and cleavage sites for the restriction enzymes EcoRI at one terminal and HindIII at the other terminal of the polylinker DNA sequence. The unique recognition and cleavage sites for the restriction enzymes BalI, and HpaI and EcoRV of the plasmid vector are located in the tetracycline resistance gene region, and the unique recognition and cleavage sites for the restriction enzymes PvuI, BglI, and BanI of the plasmid vector are located in the ampicillin resistance gene region.

The chimeric plasmid vector according to the present invention is constructed by enzymatically cleaving the plasmid pAMα1 of *Streptococcus faecalis* DS5 and the vector pACYC177 of *E. coli* so that the tetracycline resistance gene region (Tc) and the first DNA replication origin (OripAMα1) are contained in the DNA fragment derived from the plasmid pAMα1 and the ampicillin resistance gene region (Amp) and the second DNA replication origin (Ori177) are contained in the DNA fragment derived from the vector pACYC177. The two DNA fragments are ligated together with a polylinker region having the recognition and cleavage sites for the restriction enzymes EcoRI and HindIII at the opposite terminals of the polylinker sequence. Examples of the chimeric plasmid vector thus obtained have a molecular weight of about 3.0 magadaltons and are named pHY300PLK, pHY301PLK and pHY302PLK.

As discussed above, a chimeric plasmid vector according to the present invention is characterized in that it contains tetracycline and ampicilline resistance gene regions carried on its DNA and is for this reason capable of conferring a resistance to tetracycline on the host cell by transformation of *B. subtilis*. This capability of the chimeric plasmid vector provides a selective marker which is operable, in the process of transformation, for the detection and selection of the transformant, vis., the strain carrying the recombinant plasmid into which the desired foreign DNA has been introduced.

The chimeric plasmid vector according to the present invention is further characterized in that the sole recognition and cleavage sites for the restriction enzymes BalI, HpaI and EcoRV of the plasmid vector are located in the tetracycline resistance gene region, and the sole recognition and cleavage sites for the restriction enzymes PvuI, and BanI of the plasmid vector are located in the ampicilline resistance gene region. Thus, when such a chimeric plasmid vector is to be cleaved with any of these restriction enzymes, the plasmid vector could not be cut into numerous fragments at unwanted sites of the DNA. Any desired foreign DNA can therefore be inserted into the plasmid vector at selected recognition and cleavage sites of the vector.

A chimeric plasmid vector according to the present invention is further characterized by the presence therein of a polylinker region bearing a considerable number of operable cloning sites, terminal ones of which are identified as the recognition and cleavage sites for the restriction enzymes EcoRI at one terminal and HindIII at the other terminal of the polylinker DNA sequence. This will contribute to further improvement of the utility of the chimeric plasmid vector to be used as a cloning vector.

Furthermore, a chimeric plasmid vector according to the present invention has been found to be capable of replicating stably not only in *E. coli* but also in *B. subtilis* due to favorable interaction between the two particular replication origins (OripAMα1, Ori177) derived from the plasmid pAMα1 and vector pACYC177. The chimeric plasmid vector can therefore be used advantageously as a shuttle vector to reciprocate between the hosts of *E. coli* and *B. subtilis* and provides substantially equal transformation efficiencies for these host bacteria.

As well known, the most advanced of the DNA cloning host-vector systems which are presently under research and development is the EK system which consists of Gram-negative *E. coli* K-12 strain and its plasmid or phage vector. Such a host-vector system is useful for the cloning or expression of certain kinds of genes derived from the Gram-negative strain and certain kinds of genes derived from Gram-positive bacteria such as *B. subtilis*. When used for the cloning or expression of the genes derived from Gram-positive bacteria, the EK host-vector system still has far more problems to be circumvented than those concomitant with the system for the cloning or expression of the genes derived from the Gram-negative strain Various attempts are being thus made to overcome such difficulties attending the host-vector systems used for the cloning or expression of the genes derived from Gram-negative bacteria.. These attempts center on the host-vector system using *B. subtilis*, one of the most useful microorganisms as host bacteria, and involve analysis into the genetic mechanism of *B. subtilis* and development of cloning systems using the *B. subtilis* which exhibits microbiological behaviors drastically differing from those of *E. coli*. Development of an established host-vector system using *B. subtilis* is under these circumstances a most impending demand from the related industry.

As discussed previously, the chimeric plasmid vector proposed by the present invention has a relatively small molecular weight of about 3.0 megadaltons and is operable as a shuttle vector capable of reciprocating between *E. coli* which is typical of the Gram-negative bacteria and *B. subtilis* which is typical of the Gram-positive bacteria. Such a shuttle vector is expected to provide a step forward to the establishment of a cloning system using *B. subtilis* as the host bacterium and will thus prove useful for various industrial purposes.

The above chimeric plasmid vector according to the present invention is further of importance for its future prospect since the vector may be utilized extensively for the analysis into and the molecular breeding of genes of other kinds of Gram-positive bacteria belonging to, for example, the genus Lactobacillus and the genus Bifidobacterium.

More detailed description will be presented below for each chimeric plasmid in accordance with the embodiments of the present invention.

EMBODIMENT 1 CHIMERIC PLASMID, pHY780

(1)

Preparation of pACYC177

*E. coli* K12 WA802r$^-$m$^-$ (pACYC177) (owned by Dr. H. Saito, Research Institute for Applied Microorganisms, Tokyo University) was cultivated overnight in L-broth (A broth produced by adjusting the pH value of the mixture containing 1% of bactotrypton, 0.5% of yeast extract, 0.5% of NaCl, 0.1% of glucose, to 7.0 employing 1N-NaOH). The cultivated bacteria were harvested by centrifugation before they were twice washed with 100 ml of 20 mM Tris-10 mM EDTA (pH 8.0). The washed bacteria were resuspended in 9 ml of 20 mM Tris-10 mM EDTA. Lysozyme and RNase were added to the suspension by the quantity which is enough to make 100 $\mu$g/ml and 50 $\mu$g/ml respectively, before lysing reaction is allowed to occur at 0° C. for 10 minutes. The bacteria which were subjected to the aforementioned lysing reaction were added with 1 ml of 2% SDS and were further lysed at 37° C. for 5 minutes. After being kept at 0° C. for 10 minutes, the solution was centrifuged at 36,000 rpm for 30 minutes to collect the supernatant thereof.

The cesium chloride-ethidium bromide density gradient centrifugation was applied to the supernatant or a DNA crude sample of the desired DNA, for the purpose to obtain the desired DNA out of the DNA crude sample.

For this purpose, to the DNA crude sample was added the crystalline cesium chloride in a quantity identical to that of the DNA crude sample and with 0.7 ml of ethidium bromide having the concentration of 5 mg/ml to prepare a solution containing the desired cccDNA, pACYC177. The solution was centrifuged twice with 36,000 rpm for 40 hours to collect the cesium chloride fractions containing the desired cccDNA.

The collected cesium chloride fractions containing the desired cccDNA were washed with isopropanol saturated with cesium chloride to exclude ethidium bromide. The cccDNA dissolved in the cesium chloride solution was dialysed against a buffer A containing 10 mM tris-0.1 mM EDTA and having the pH value of 7.4, before the dialysed cccDNA dissolved in the buffer A phenol saturated with the same buffer was added in a quantity sufficient to double the entire volume. The mixture was shaken to allow a small quantity of protein to be denatured, before the protein was allowed to travel to the boundary portion sandwiched between two liquid layers, the upper layer containing the desired cccDNA and the lower layer consisting of the phenol, which were separated from each other by centrifugation for the purpose to collect the desired cccDNA. The upper layer was further dialysed against the buffer A to exclude the phenol which contaminated the desired cccDNA, to purify the desired cccDNA, pACYC177.

By the foregoing processes, pACYC177 whose cleavage map is shown by (A) in FIG. 1(A) was prepared.

(2) Preparation of pAM$\alpha$1

*S. faecalis* DS5 (ATCC14508) was cultivated overnight in the Rogosa's medium (a medium having the pH value of 6.8 and of which 1 liter contains 20 g of glucose, 10 g of trypticase peptone, 5 g of yeast extract, 3 g of tryptose, 3 g of K$_2$HPO$_4$, 3 g of KH$_2$PO$_4$, 2 g of ammonium citrate, 1 g of sodium acetate, 1 g of Tween 80, 0.575 g of MgSO$_4$.H$_2$O, 0.5 g of L-cystine hydrochloride, 0.12 g of MnSO$_4$.2H$_2$O 84 mg of FeSO$_4$.7H$_2$O).

Processes similar to those which had been described above in (1) of this section for preparation of pACYC177, were employed to collect the DNA crude sample of DNA-s retained by *S. faecalis*.

The DNA sample which had been obtained from the DNA crude sample employing cesium chloride-ethidium bromide density gradient centrifugation, was further applied to sucrose density gradient centrifugation for the purpose of selectively obtaining the desired cccDNA, pAM$\alpha$1 from the mixture containing pAM$\beta$1 and pAMΓ1 other than pAM$\alpha$1.

Namely, 0.5 ml of the DNA sample was put on 12 ml of sucrose solution having the 5–30% density gradient which was prepared in a nitrocellulose tube. The buffer which was employed in this process, was a mixture of 50 mM Tris-50 mM EDTA-50 mM NaCl, (pH 8.0). Centrifugation was employed at 10° C. with 20,000 rpm for 16 hours to split the DNA sample to a plurality of DNA groups each of which contains a part of the DNA sample having a specific molecular weight. To individually collect each of the DNA groups, an opening was produced at the bottom of the nitrocellulose tube and a plurality of fractions consisting of 10 drops were collected. 0.8%-agarose gel electrophoresis process was applied to 10 μl each of the aforementioned fractions for the purpose to determine the molecular weight of the DNA-s contained in the specific fraction. The fractions containing the DNA-s having the molecular weight of 6 Md were selectively collected, before they were dialysed against the buffer A.

In this manner, pAMα1 whose cleavage map was shown by (B) in FIG. 1(A), was prepared.

(3) Cleavage of pACYC177 and pAMα1 and ligation of the cleaved DNA fragments of pACYC177 and pAMα1

1 μl of a buffer (a mixture containing 100 mM of Tris-HCl having the pH value of 7.6, 70 mM of MgCl$_2$, 70 mM of β-mercaptoethanol and 500 mM of NaCl) and 1 μl HindIII having the activity of 4 units μl were dropped in 10 μl each of the DNA solution (containing 0.1–0.2 μg of the DNA-s) produced and collected employing the foregoing processes described in (1) and (2), to allow HindIII to digest the DNA-s at 37° C. As a result, the both DNA-s contained in the aforementioned DNA solution (pACYC177 and pAMα1) were recognized and cleaved at the recognition and cleavage site of HindIII. After duration of the digestion for 60 minutes, the mixture was heated at 60° C. for 10 minutes to terminate the digestion. After the mixture had added thereto 5 M of NaCl at 1/50 of the volume and further had added thereto ethanol at the temperature of −20° C. in a quantity twice the entire quantity of the mixture, it was kept at −20° C. for 30 minutes. After the mixture was centrifuged at 0° C. with the speed of 15,000 rpm for 5 minutes, the precipitate was collected, before it was washed with ethanol at −20° C. After the washed precipitate was centrifuged at 0° C. with 15,000 rpm for 2 minutes, it was entirely dried.

The DNA fragments acquired by the foregoing process were dissolved in 20 μl of sterilized water. The water containing the DNA fragments was added with a mixture containing 3 μl of 10 mM ATP, 3 μl of 100 mM dithiothreitol, 3 μl of 660 mM Tris-HCl (pH 7.6)-66 mM MgCl$_2$ and 0.5 μl of T4 ligase having the activity of 400 units/μl. Ligated in this process were a linear DNA fragment which was produced by allowing HindIII to digest pACYC177 and each of two linear DNA fragments, smaller one and larger one, which were produced by allowing the same restriction enzyme to digest pAMα1. After this ligation process was allowed to occur at 15° C. overnight, 120 μl of sterilized water poured, the entire quantity was increased to 150 μl. (4) Transformation of Escherichia coli E. coli K12 C600r−m− (owned by Dr. H. Saito, Research Institute for Applied Microorganisms, Tokyo University) was cultivated overnight in L-broth. 0.05 ml of this culture was inoculated in 5 ml of L-broth, to cultivate the same microorganisms organisms on a shaker at 37° C. for 130 minutes. The culture was centrifuged to collect the cells. After the cells were washed with 0.1 M of CaCl$_2$ solution at 0° C., the washed cells were suspended in 0.25 ml of the 0.1 M CaCl$_2$ solution at 0° C. to produce competent cells of the aforementioned microorganisms. 0.1 ml each of the competent cells and the ligated DNA-s produced employing the foregoing process described in (3), were put together with each other and kept at 0° C. for 5 minutes to allow the competent cells to be transformed with the aforementioned ligated DNA-s. The transformants were cultivated at 37° C. for one hour in 1-ml of a culture containing 0.8 ml of L-broth. The culture was applied to a medium containing L-broth as well as agar, tetracycline and ampicillin in the respective quantity of 1.5% of the L-broth volume, 20 μg/ml and 30 units/ml, to be cultivated overnight at 37° C. for the purpose to inspect that the transformants had actually obtained the resistance against tetracycline and/or ampicillin. Since the transformants were successfully cultivated on the medium containing tetracycline and ampicillin, it was determined that the transformants had readily obtained the resistance against tetracycline and ampicillin. 10 colonies which grew on the medium containing tetracycline and ampicillin were picked up, and the picked up transformants were subjected to a series of examinations described below to determine the dimension of the plasmid DNA retained therein. (5)

Extraction of the retained plasmid DNA and measurement of the molecular weight thereof The aforementioned transformants were cultivated overnight in L-broth. Centrifugation was applied to 5 ml of the culture to selectively collect the transformants. The separated transformants were suspended in 0.5 ml of 50 mM Tris-10 mM EDTA (pH 7.4). This suspension was added with 0.2 ml of a mixture containing 2 mg/ml of lysozyme and 0.5 mg/ml of RNase to lyse the transformants at 37° C. for 5 minutes. The solution has further added thereto 0.2 ml of 2% SDS solution to further lyse the transformants completely at 30° C. for 1 through 2 minutes. After being kept at 0° C. for 10 minutes, this solution was centrifugated at 0° C. with 20,000 rpm for 10 minutes. 0.5 ml of the supernatant was carefully mixed with 0.5 ml of phenol saturated with buffer A to allow the undesired protein to be denatured with the phenol. The mixture was centrifuged at the room temperature with 15,000 rpm for 3 minutes, and the upper layer which was separated from the lower layer was collected. 50 μl of the collected upper layer was subjected to electrophoresis process on a 0.8%-agarose gel to determine the molecular weight of the plasmid DNA retained in each transformant.

The aforementioned sequential process for determination of the molecular weight of a material was applied to 10 independent colonies of the transformants. The results showed the molecular weight of the plasmid DNA was approximately 7.8 Md.

In this manner, a new chimeric plasmid whose cleavage map was shown by (C) in FIG. 1(A) was synthesized from pACYC177 whose cleavage map was shown by (A) in FIG. 1(A) and pAMα1 whose cleavage map was shown by (B) in FIG. 1(A). This new chimeric plasmid was named pHY780. Another chimeric plasmid which was simultaneously synthesized in the same process was named pHY11.

The foregoing description has clarified that pHY780 is allowed to enjoy stable replications and expression of genetic information thereof at least in E. coli.

Ligation of the DNA fragments of pACYC177 and of pAMα1 produces two independent chimeric plasmids, pHY780 and pHY11 of which the molecular weigh is same, due to alternative directions in which the DNA fragments are ligated. However, a cleaving process by means of BamHI allows the two independent chimeric plasmids to be sorted from each other, because the BamHI cleaving process produces two independent groups each of which has the dimension different from each other.

Further investigation was carried out for a variety of restriction enzymes which can be employed for removal of a portion or portions of each of pHY780 and pHY11 without losing at least both of the origins, OripAMα1 and Ori177, and also without causing any damage to two independent genes, (Tc) and (Amp). A larger variety of restriction enzymes available for pHY780, made it reasonable to choose pHY780, because this allowed easier shortening processes to follow.

EMBODIMENT 2 CHIMERIC PLASMID, pHY600

(1) Cleavage of pHY780 and ligation of the cleaved DNA fragment of pHY780

A transformed $E.\ coli$ C600r⁻m⁻ (pHY780) produced in EMBODIMENT 1, was subjected to an extraction process similar to that which had been described in (5) for EMBODIMENT 1, for the purpose to extract the retained plasmid DNA.

2 μl of a buffer (a mixture containing 100 mM of Tris-HCl having the pH value of 7.6, 70 mM of $MgCl_2$, 70 Mm of β-mercaptoethanol and 500 mM of NaCl) and BamHI of 4 units were dropped in 1μg/20 μl of the extracted DNA, and BamHI was allowed to digest the extracted DNA at 37° C. After duration of the digestion for 60 minutes, the digested DNA was heated at 60° C. for 10 minutes to terminate the digestion. After the digested DNA had added thereto 80 μl of water, 2 μl of 5 M NaCl and 200 μl of ethanol at the temperature of −20° C., it was kept at −20° C. for 30 minutes. The digested DNA was centrifuged at 0° C. with 10,000 rpm for 5 minutes to collect a desired DNA. After the collected DNA was washed with 200 μl of ethanol at −20° C., the DNA dried. The dried DNA was dissolved in 20 μl of water, and was ligated employing T4 ligase in the similar manner as was described in (3) for EMBODIMENT 1.

(2) Transformation of Escherichia coli $E.\ coli$ C600r⁻m⁻ was transformed with the aforementioned plasmid DNA. the transformants showed the resistance against tetracycline having the concentration of 20μg/ml and against ampicillin having the concentration of 30 units/ml.

A sequential process for determination of the molecular weight of the DNA-s retained in the transformants, which was similar to that which had been described in (5) for EMBODIMENT 1, was applied to 10 independent colonies of the aforementioned transformants. The results showed the molecular weight of any of the plasmids was approximately 6 Md.

In this manner, a new chimeric plasmid whose cleavage map was shown by (D) in FIG. 1(B) was synthesized from pHY780 whose cleavage map was shown by (C) in FIG. 1(A). This new chimeric plasmid was named pHY600.

The results of the foregoing processes have clarified that pHY660 is allowed to function as a cloning vector at least for $E.\ coli$.

EMBODIMENT 3 CHIMERIC PLASMID, pHY460

(1) Cleavage of pHY600 and ligation of the cleaved fragment of pHY600 A process similar to that which had been described in (3) for EMBODIMENT 1 was employed to allow the restriction enzymes XhoI and SalI to cleave pHY600, the product of EMBODIMENT 2, and to allow T4 ligase to ligate the cleaved DNA fragment thereof. A process similar to that which had been described in (4) for EMBODIMENT 1 was employed to transform $E.\ coli$ with the ligated DNA and to produce a chimeric plasmid, which has the molecular weight of approximately 4.6 Md.

In this manner, a new chimeric plasmid whose cleavage map was shown by (E) in FIG. 1(B) was synthesized from pHY600 whose cleavage map was shown by (D) in FIG. 1(B). This new chimeric plasmid was named pHY460. (2)

Transformation of Bacillus subtilis (i) Preparation of competent cells $B.\ subtilis$ Marburg 168 (owned by Dr. H. Saito, Research Institute for Applied Microorganisms, Tokyo University) was cultivated on an L-broth agar plate overnight. The cultivated microorganisms were inoculated in medium I, that is Spizizen minimal medium (a mixture containing 1.4% of $K_2HPO_4$, 0.2% of $(NH_4)_2SO_4$, 0.1% of sodium citrate, 0.02% of $MgSO_4 \cdot 7H_2O$, 0.5% of glucose, 0.02% of casein hydrolysate, 0.2% of yeast extract and 50 μg/ml of L-tryptophane, and was cultivated on a shaker at 37° C. for approximately 4 hours until the cultivation arrives at the stationary phase. Medium II (a medium similar to medium I excepting that the density of L-tryptophane and yeast extract are 5 μg/ml and 0.02% respectively and 5 mM of $MgSO_4$ is added) was employed to decrease the concentration of the cultivated cells to 1/10, before the cultivation was continued. A 90-minute period was needed to allow the cells to be converted into competent ones. 0.9 ml of this competent cells were added with 0.1 ml of the DNA solution of the chimeric plasmid pHY460 produced above in the EMBODIMENT and were cultivated on a shaker at 37° C. for 90 minutes.

The abovementioned cultivation process allowed the competent cells to be transformed with the DNA to express the genetic information thereof. (ii)

Detection of transformant the transformants retaining the plasmid DNA (pHY460) were applied on an L-agar plate containing tetracycline by 20 μg/ml, and were cultivated at 37° C. for 24 hours. A process similar to that which had been described for description of EMBODIMENT 1 was applied to some of the colonies acquired above, for the purpose to determine the dimension of a plasmid DNA retained in each transformant. As a result, the molecular weight of the chimeric plasmid produced by the aforementioned process was determined to be approximately 4.6 Md.

$E.\ coli$ C600r⁻m⁻ was also determined to have been transformed, by means of a process similar to that which was described in (5) for EMBODIMENT 1.

The foregoing description has clarified that the chimeric plasmid pHY460 is allowed to function as a shuttle vector for a host-vector system employing at least $E.\ coli$ and $B.\ subtilis$.

The transformed $E.\ coli$ (pHY460) and the transformed $B.\ subtilis$ (pHY460) produced in this EMBODIMENT, were deposited at Fermentation Research Institute Agency of Industrial Science and Technology, and the former was given the deposition No. FERM BP-438 and the latter was given the deposition No. FERM BP-439.

EMBODIMENT 4 CHIMERIC PLASMID, pHY360

A process similar to that which had been described in (3) for EMBODIMENT 1 was employed to allow the restriction enzymes SacII and BstEII to produce DNA fragments having a pair of cohesive ends by cleaving pHY460, the product of EMBODIMENT 3, and the produced DNA fragments were digested with S1 nuclease to convert both cohesive ends of each of the fragments into flush ends by nipping off a single stranded DNA chain protruding at each end of the same fragment, before the both flush ends were ligated by T4 ligase to produce a circular DNA.

The abovementioned S1 nuclease digestion was carried out by S1 nuclease having the activity of 50 units /μl at 37° C. for 5 minutes in an S1 reaction buffer containing 30 mM of sodium acetate (pH 4.6), 50 mM of NaCl, 1 mM of ZnSO$_4$ and 5% of glycerol.

A process similar to that which had been described in (4) EMBODIMENT 1 was employed to transform *E. coli* C600r$^-$m$^-$ with the plasmid DNA (pHY360) produced above, for the purpose to produce a transformant having the resistance against tetracycline and ampicillin.

A process similar to that which had been described in (5) for EMBODIMENT 1 was employed to determine the dimension of the plasmid DNA retained in the transformant produced above. The results showed that all the transformants had the molecular weight of approximately 3.6 Md.

A process similar to that which had been described in (2) for EMBODIMENT 3 was employed to produce a variety of transformants of *B. subtilis*.

In this manner, a new chimeric plasmid whose cleavage map was shown by (F) in FIG. 1(B) was synthesized from pHY460 whose cleavage map was shown by (E) in FIG. 1(B). This new chimeric plasmid was named pHY360.

The aforementioned aquisition of the transformant has proved that this pHY360 is allowed to function as a cloning vector (a shuttle vector) at least both for *E. coli* and for *B. subtilis*.

The transformed *E. coli* (pHY360) and the transformed *B. subtilis* (pHY360) were deposited at Fermentation Research Institute Agency of Industrial and Technology, and the former was given the deposition No. FERM BP-443 and the latter was given the deposition No. FERM BP-441.

EMBODIMENT 5 CHIMERIC PLASMID, pHY310

A process similar to that which had been described in (3) for EMBODIMENT 1 was employed to allow the restriction enzymes AccI and BamHI to cleave pHY360, the product of EMBODIMENT 4.

the reaction mixture containing the cleaved DNA fragments was added with T4 DNA polymerase and deoxyribonucleoside triphosphate to convert the both cohesive ends of each of the DNA fragments into the flush ends by patching up the vacant sequence complementary to that of a single stranded DNA chain protruding at each end of the same fragment. Namely, the abovementioned reaction was carried out at 37° C. for 15 minutes in the mixture of T4 DNA polymerase having the activity of 1 unit, 25 μM each of 4 kinds of deoxyribonucleoside triphosphate and 20 μl of a buffer having the pH value of 8.0 and containing 67 mM of Tris-HCl, 6.7 mM of MgCl$_2$, 6.7 mM of β-mercaptoethanol. The following ligation process in which T4 legase and HindIII linker (dpCAAGCTTG) (produced by Takara Shuzo Co., Ltd) having the optical density of 0.01 OD were added, allowed the HindIII linker to bridge the both flush ends of the linear DNA fragment produced in the above process for the purpose to produce a circular DNA.

A process similar to that which had been described in (4) for EMBODIMENT 1 was employed to transform *E. coli* with the aforementioned ligated circular DNA. Produced by the process was a transformant having the resistance against tetracycline and ampicillin.

Processes similar to those which had been described for (5) for EMBODIMENT 1 were employed to determine the molecular weight and the recognition and cleavage site for the bridging HindIII linker. The results showed that the approximate molecular weight of the plasmid DNA extracted from the transformant was 3.1 Md and that the same DNA can be cleaved by HindIII.

In this manner, a new chimeric plasmid whose cleavage map was shown by (F') in FIG. 4 was synthesized from pHY360 whose cleavage map was shown by (F) in FIG. 4. This new chimeric plasmid was named pHY310.

As were in the cases of pHY460 and pHY360, this pHY310 was determined to have a function to frequently transform also *B. subtilis*.

The transformed *E. coli* (pHY310) and the transformed *B. subtilis* (pHY310) were deposited at Fermentation Research Institute Agency of Industrial Science and Technology. The former was given the deposition No. FERM BP-436 and the latter was given the deposition No. FERM BP-437.

EMBODIMENT 6 CHIMERIC PLASMID, pHY385

A process similar to that which had been described in (2) for EMBODIMENT 3 was employed to transform *B. subtilis* with pHY460. The transformants picked up from some of colonies were cultivated separately in L-broth at 37° C. for 50 successive generations. As in the case of (2) for EMBODIMENT 3, the later cultivations were carried out on an L-agar plate medium containing 20 μg/ml of tetracycline.

A process similar to that which had been described in (5) for EMBODIMENT 1 proved that the colony which had been obtained by the above cultivation contained a plasmid DNA.

As a result, the plasmid DNA-s having the molecular weight of 3.85 Md were found in 4 colonies of transformants out of 36 colonies thereof. Further efforts were used to analyze the structure of this plasmid DNA. The results showed that this plasmid DNA was a new chimeric plasmid which had been produced from pHY460 by deleting the 0.75 Md DNA fragment therefrom.

In this manner, a new chimeric plasmid whose cleavage map was shown by (G) in FIG. 1(B) was obtained from pHY460 whose cleavage map was shown by (E) in FIG. 1(B). This new chimeric plasmid was named pHY385.

A process similar to those which had been described in (4) and (5) for EMBODIMENT 1 proved that *E. coli* C600r$^-$m$^-$ had been transformed with pHY385. This means that this pHY385 is allowed to function as a cloning vector in the host-vector system at least both for *E. coli* and for *B. subtilis*.

The transformed *E. coli* (pHY385) and the transformed *B. subtilis* (pHY385) were deposited at Fermentation Research Institute Agency of Industrial Science and Technology. The former was given the deposition No. FERM BP-444 and the latter was given the deposition No. FERM BP-442.

EMBODIMENT 7 CHIMERIC PLASMID, pHY340

A process similar to that which had been described in (3) for EMBODIMENT 1 was employed to allow the restriction enzyme HaeII to cleave pHY385, the product of EMBODIMENT 6, and to allow T4 ligase to ligate the cleaved DNA fragment.

A process similar to that which had been described in (4) for EMBODIMENT 1 was employed to transform *E. coli* C600r−m− with the plasmid DNA (pHY340) produced above, for the purpose to produce a transformant having the resistance against tetracycline and ampicillin.

A process similar to that which had been described in (5) for EMBODIMENT 1 was employed to determine the dimension of the plasmid DNA-s retained in the transformants produced above. The results showed that all the transformants had the plasmid DNA, the approximate weight of which was 3.4 Md.

A process similar to that which had been described in (2) for EMBODIMENT 3 was employed to produce a variety of transformants of *B. subtilis*.

In this manner, a new chimeric plasmid whose cleavage map was shown by (G') in FIG. 2 was synthesized from pHY385 whose cleavage map was shown by (G) in FIG. 2. This new chimeric plasmid was named pHY340.

The aforementioned reciprocal transformation processes have proved that this pHY340 was allowed to function as a cloning vector (a shuttle vector) at least both for *E. coli* and for *B. subtilis*.

The transformed *E. coli* (pHY340) and the transformed *B. subtili* (pHY340) were deposited at Fermentation Research Institute Agency of Industrial Science and Technology. The former was given deposition No. FERM BP-445 and the latter was given the deposition No. FERM BP-446.

EMBODIMENT 8 CHIMERIC PLASMID, pHY330 pHY460, the product of EMBODIMENT 3, was cleaved by the restriction enzyme XbaI. After being treated with S1 nuclease, the cleaved DNA fragments were ligated by T4 ligase to synthesize a chimeric plasmid. Namely, 0.5 μg/50 μl of the plasmid DNA (pHY460) had been stored at 4° C. in buffer A for 4 months, for the purpose of allowing each of the plasmid DNA-s to incur "nicks" at random locations thereof and for the ultimate purpose of selectively producing a circular DNA having a desired dimension by ligating a variety of DNA fragments which were shortened in random length.

The plasmid DNA-s having "nicks" were cleaved by the restriction enzyme XbaI having the activity of 4 units dissolved in a buffer containing 10 mM of Tris-HCl(pH 7.6), 7 mM of $MgCl_2$, 7 mM of β-mercaptoethanol and 50 mM of NaCl. The buffer containing the cleaved DNA fragments had added thereto NaCl in a volume sufficient to adjust the NaCl concentration to 100 mM and with the cold ethanol in the quantity twice that of the foregoing concentration modulated buffer, to be cooled at −20° C. The DNA fragments were collected by the 3- minute treatment at 4° C. with the 15,000 rpm centrifugation, before being washed by the cold ethanol. After ethanol was evaporated, the DNA fragments were dissolved in 50 μl of S1 buffer containing 30 mM of sodium acetate (pH 4.6), 50 mM of NaCl, 1 mM of $ZnSO_4$ and 5% glycerol for the purpose of allowing S1 nuclease to cleave each of the DNA fragments at "nicks" where it was selectively subjected to the digestion by S1 nuclease due to the single stranded structure thereof.

The DNA fragments were subjected to the reaction with 0.5 μl of S1 nuclease having the activity of 500 units/μl at 37° C. for 5 minutes. This reaction mixture had added thereto 100 μl of phenol saturated with buffer A. After being agitated, the mixture was centrifuged at the room temperature with 15,000 rpm for 3 minutes, to collect the upper layer containing the DNA fragments.

The NaCl concentration of the solution taken out of the upper layer was adjusted to 100 mM. This solution was cooled at −20° C. ethanol for 30 minutes, before being centrifuged at 4° C. with 15,000 rpm for 3 minutes to collect the precipitate. After the precipitate was washed with the cold ethanol, the ethanol as evaporated.

The DNA precipitated at the bottom of the centrifuge tube was dissolved in 20 μl of water, before being added with 3 μl of 10 mM ATP, 3 μl of 100 mM dithiothreitol and 3 μl of 660 mM Tris-HCl(pH 7.6)−6.6 mM $MgCl_2$. T4 ligase having the activity of 10 units was allowed to ligate the DNA fragments at 15° C.

The ligated DNA was added with water of 170 μl which is enough to make the volume 200 μl. A process similar to that which had been described in (4) for EMBODIMENT 1 was employed to transform 100 μl of competent cells which had been produced by treating *E. coli* C600r−m− with $CaCl_2$, with 100 μl of the DNA solution. A process similar to that which had been described in (5) for EMBODIMENT 1 was employed to extract the remained plasmid DNA whose molecular weight is approximately 3.3 Md from the transformants.

In this manner, a new chimeric plasmid whose cleavage map was shown by (H) in FIG. 3 was synthesized from pHY460 whose cleavage map was shown by (E) in FIG. 3. This new chimeric plasmid was named pHY330.

Further, pHY330 has been proved to be a cloning vector useful at least for *E. coli*.

EMBODIMENT 9 CHIMERIC PLASMID, pHY285

Process similar to that which had been described in (3) through (5) for EMBODIMENT 1 was employed to cleave pHY330, the product of EMBODIMENT 8, employing the mixture containing the restriction enzyme HaeII in a buffer containing 10 mM of Tris-HCl(pH 7.6), 7 mM of $MgCl_2$ and 7 mM of β-mercaptoethanol, ligate the cleaved DNA fragments produced above and transform *E. coli* with the ligated DNA produced above, for the purpose to produce a circular DNA whose approximate molecular weight is 2.85 Md.

In this manner, a new chimeric plasmid whose cleavage map was shown by (I) in FIG. 3 was synthesized form pHY330 whose cleavage map was shown by (H) in FIG. 3. This new chimeric plasmid was named pHY285.

Further, pHY285 was proved to be a cloning vector useful at least for *E. coli*.

EMBODIMENT 10 CHIMERIC PLASMID, pHY225

The restriction enzymes SacII and EcoRI were allowed to cleave pHY285, the product of EMBODIMENT 9. As was in the case of EMBODIMENT 4 and 8, the cleaved DNA fragments were digested with S1 nuclease to convert the both cohesive ends of each of the fragments into the flush ends by nipping off a single stranded DNA chain protruding at each end of the same fragment, before the both flush ends were ligated by T4 ligase to produce a circular DNA. Namely, 0.4 μg/50 μl of the DNA (pHY285) was cleaved by SacII having the activity of 4 units dissolved in a buffer containing 10 mM of Tris-HCl (pH 7.6), 7 mM of $MgCl_2$, 7 mM of β-mercaptoethanol. The cleavaging process was carried out at 37° C. for 60 minutes, before being heated at 60° C. for 10 minutes to terminate the reaction. The reaction mixture in which the DNA-s were dissolved had added thereto NaCl in a quantity sufficient to make the concentration thereof to 40 mM, before having added thereto EcoRI having the activity of 4 units, allowing the DNA-s to be subjected to a reaction at 37° C. for 60 minutes. After being heated at 60° C. for 10 minutes, the reaction mixture had added thereto 50 μl of water.

To this mixture was added phenol saturated with buffer A and shaken, before being centrifuged at the room temperature with 15,000 rpm for 30 minutes.

The upper layer containing the DNA-s which was separated from the mixture in the abovementioned centrifugation, had added thereto NaCl in a quantity sufficient to adjust the NaCl concentration to 100 mM, before being treated with the cold ethanol. After the ethanol was evaporated, the DNA-s were treated with S1 nuclease at 37° C. for 5 minutes. A process similar to that which had been described in (3) through (5) for EMBODIMENT 1 was employed to ligate the above produced DNA fragment and to transform $E.\ coli$ with the DNA, to produce a new chimeric plasmid whose approximate weight is 2.25 Md. In the aforementioned processes, a new chimeric plasmid was synthesized from pHY285 whose cleavage map was shown by (J) in FIG. 3. This new chimeric plasmid was named pHY225. Further, pHY225 was proved to be a cloning vector at least for $E.\ coli$.

Above described chimeric plasmid pHY340 is used as a source of a plasmid vector according to a further aspect of the present invention.

Figure 5:
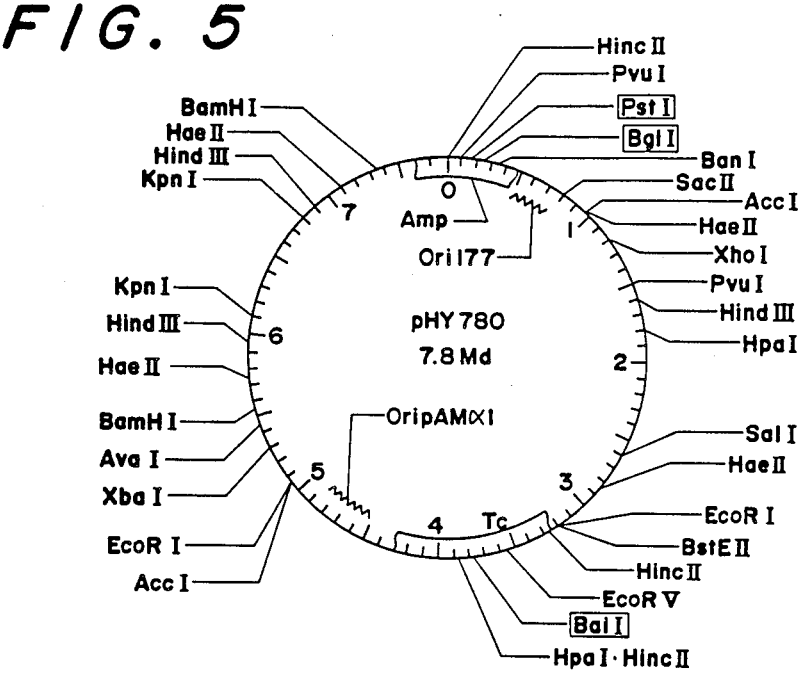
FIG. 5 is a cleavage map showing the sequence of the recognition and cleavage of chimeric plasmid pHY780 of the present invention.
Figure 6:
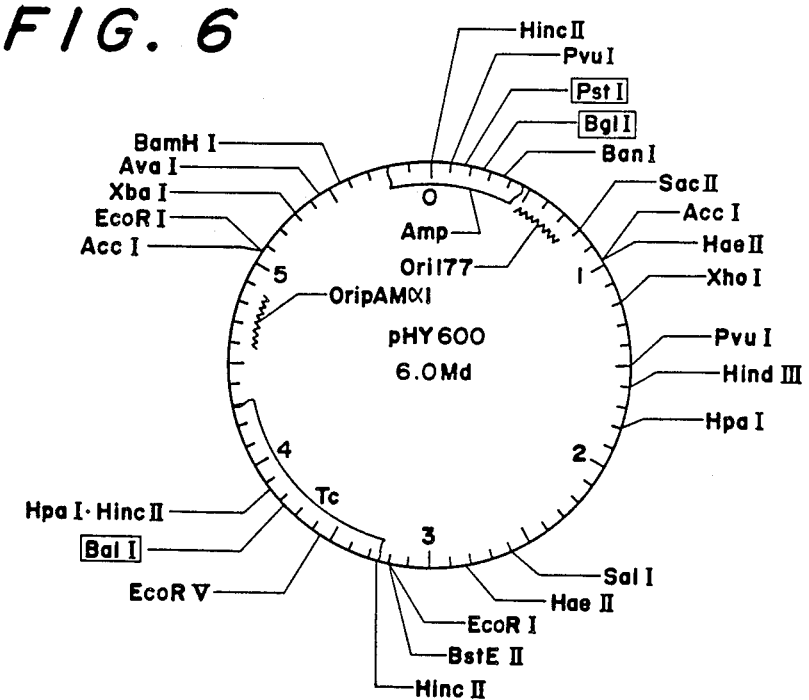
FIG. 6 is a cleavage map showing the sequence of the recognition and cleavage of chimeric plasmid pHY600 of the present invention.
Figure 15:
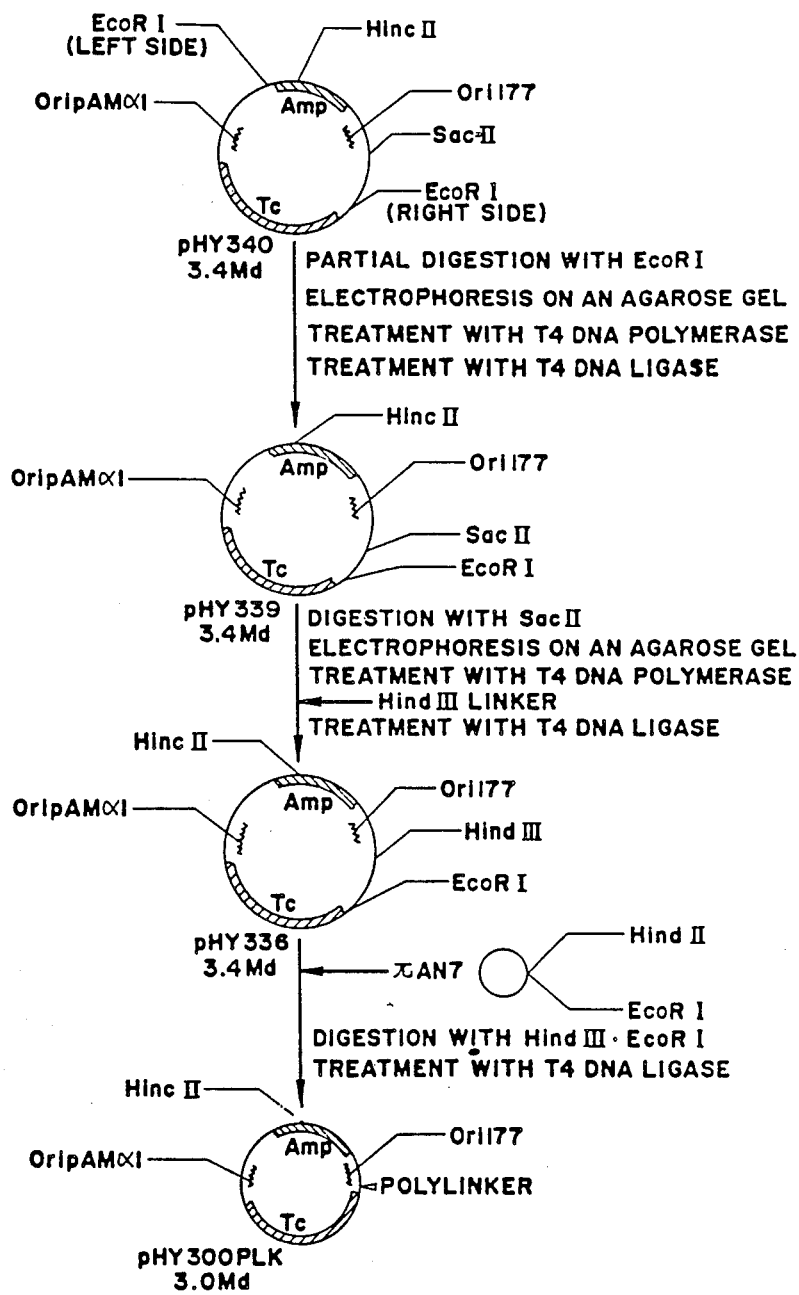
FIG. 15 is a flowchart showing the steps involved in the synthesis of a preferred example, specifically named pHY300PLK, of a chimeric plasmid vector according to the present invention.

As shown in FIG. 15 the plasmid pHY340 has a molecular weight of about 3.4 Md and contains two EcoRI sites. The circular plasmid is partially digested with EcoRI to obtain fragments each open at one (shown to the left in FIG. 15) of these two EcoRI sites. The resultant DNA fragment is subjected to low-melting-point electrophoresis on an agarose gel, whereupon the DNA having the molecular weight of 3.4 Md is extracted from the gel plate. The linear DNA thus extracted is treated with T4 DNA polymerase and T4 DNA ligase to produce circular DNA. The circular DNA is introduced into $E.\ coli$ and a plasmid is extracted from the resultant transformant. One of the synthesized plasmids, named pHY339, had the unique EcoRI and SacII sites as shown in FIG. 5 and can be cut at these two sites into two segments, the smaller one of which has a molecular weight of about 0.4 Md. The plasmid pHY339 is cleaved with SacII and the resultant linear DNA is treated with T4 DNA polymerase and, upon addition of phosphorylated HindIII linker (dpCAAGCTTG), further treated with T4 DNA ligase, thus producing a plasmid named pHY336 as also shown in FIG. 15. The plasmid pHY336 has a HindIII site in place of the SacII site in the plasmid pHY339. The section of this plasmid pHY336 which intervenes between the EcoRI and HindIII sites is excised from the plasmid and is substituted by an appropriate polylinker. The polylinker may be a DNA fragment derived from, for example, plasmid πAN7 and having a sequence of recognition and cleavage sites for restriction enzymes sequenced in the form of $$\text{EcoR}I - \begin{pmatrix} \text{Sma}I \\ \text{Xma}I \end{pmatrix} - \text{Bam}HI - \begin{pmatrix} \text{Sal}I \\ \text{Acc}I \\ \text{Hinc}II \end{pmatrix} - \text{Pst}I -$$

$$\text{Bgl}II - \text{Xba}I - \text{Hin}dIII.$$

Specific examples of such a polylinker operable in the process of preparing a chimeric plasmid vector according to the present invention include: (1) a DNA fragment having a nucliotide sequence of

5'-GAATTCCCGGGGATCCGTCGACCT-
GCAGATCTCTAGAAGCTT-3', which is characterized by the sequence of recognition and cleavage sites for restriction enzymes sequenced in the form of $$\text{EcoR}I - \begin{pmatrix} \text{Sma}I \\ \text{Xma}I \end{pmatrix} - \text{Bam}HI - \begin{pmatrix} \text{Sal}I \\ \text{Acc}I \\ \text{Hinc}II \end{pmatrix} - \text{Pst}I -$$

$$\text{Bgl}II - \text{Xba}I - \text{Hin}dIII.$$

(2) a DNA fragment having a nucleotide sequence of

5'-GAATTCCCGGGGATCCGTCGACCT-
GCAGCCAAGCTT-3', which is characterized by the sequence of recognition and cleavage sites for restriction enzymes sequenced in the form of $$\text{EcoR}I - \begin{pmatrix} \text{Sma}I \\ \text{Xma}I \end{pmatrix} - \text{Bam}HI - \begin{pmatrix} \text{Sal}I \\ \text{Acc}I \\ \text{Hinc}II \end{pmatrix} - \text{Pst}I - \text{Hin}dIII$$

and (3) a DNA fragment having a nucleotide sequence of

5'-GAATTCGAGCTCGCCCGGGGATCCT-
CTAGAGTCGACCTGCAGCCCAAGCTT-', which is characterized by the sequence of recognition and cleavage sites for restriction enzymes sequenced in the form of $$\text{EcoR}I - \text{Sst}I - \begin{pmatrix} \text{Sma}I \\ \text{Xma}I \end{pmatrix} - \text{Bam}HI - \text{Xba}I -$$

$$\begin{pmatrix} \text{Sal}I \\ \text{Acc}I \\ \text{Hinc}II \end{pmatrix} - \text{Pst}I - \text{Hin}dIII.$$

It may however be remembered that these examples of the polylinker operable for the preparation of a chimeric plasmid vector according to the present invention are merely for the purpose of description and are not limitative of the scope of the invention.

The above-described further aspect of the present invention will be better understood from the following Examples.

Example 1

(1) Preparation of Plasmid pHY339 (Removal of one of the EcoRI sites from plasmid pHY340)

Five point seven μl of a 10-fold concentrated buffer containing 100 mM Tris-HCl (pH 7.6), 70 mM MgCl$_2$, 70 mM β-mercaptoethanol and 500 mM NaCl was added to 53 μl of pHY340 DNA (100 μl/ml), followed by addition of 2 μl of 6 unit/μl EcorI. The mixture of these was divided into three equal fractions, which were incubated at 37° C. for 15, 20 and 25 minutes, respectively, to digest the DNA in each fraction with EcoRI. Each of the fractions was heated at 70° C. for 5 minutes to terminate the reaction and was thereafter electrophoresed on a 1 percent low-melting-point agarose slab gel (available from Bethesda Research Laboratories, Inc., USA) containing 1 μl/ml of ethidium bromide. The linear DNA of the molecular weight of 3.4 megadaltons with a break at one of the EcoRI sites was recovered from the gel plate and was melted in a water bath at 65° C. after addition of two volumes of a buffer containing 40 mM Tris, 20 mM sodium acetate and 1 mM 2Na-EDTA (disodiumethylenediaminetetraacetate). The resultant preparation was allowed to cool at room temperature and was thereafter mixed with an equal volume of phenol, followed by vigorous shaking. The mixture was subjected to centrifugation at 15,000 rpm for 3 minutes at room temperature and the aqueous layer containing DNA was recovered therefrom. The DNA solution was mixed with an equal volume of phenol and the above described procedure was repeated to collect a DNA-containing aqueous solution for a second time. Two hundred μl of a buffer (pH 8.0) containing 50 mM Tris, 10 mM EDTA (ethylenediaminetetraacetic acid), and 100 mM NaCl was added to the DNA solution. The resultant mixture was mixed with two volumes of cold ethanol of −20° C. and was chilled at −20° C. for 30 minutes. After cooling, the mixture was centrifuged at 15,000 rpm at 0° C. for 5 minutes and the precipitates of DNA were washed with ethanol of −20° C. for 2 minutes and the super-natant ethanol was discarded by decantation, whereupon the residue of the ethanol in the DNA precipitates was evaporated completely. The DNA fragments thus obtained were dissolved in 5 μl of sterile water. To the resultant aqueous solution of DNA were added 2 μl of a 10-fold concentrated T4DNA polymerase buffer (containing 670 mM Tris-HCl (pH 8.0), 67 mM MgCl$_2$ and 70 mM β-mercaptoethanol), 8 μl of sterile water, and 0.8 μl of 2.5 mM deoxyribonucleoside triphosphates (dATP, dGTP, dCTP and TTP), followed by further addition of 0.5 μl of 4 unit/μl T4 DNA polymerase. The mixture was incubated at 37° C. for 15 minutes. Then, 200 μl of a solution containing 50 mM Tris, 10 mM EDTA and 100 mM NaCl and further phenol were added to the reaction mixture to inactivate the enzymes contained therein. DNA fragments were then recovered following the above described ethanol precipitation procedure. The DNA fragments thus obtained were dissolved in 20 μl of sterile water, to which were added 3 μl of 10 mM ATP, 3 μl of 3 μl of 100 mM dithiothreitol, and 3 μl of a buffer consisting of 660 mM Tris-HCl (pH 7.6) and 66 mM MgCl$_2$, and further 1 μl of 3 unit/μl T4 DNA ligase. The resultant preparation was incubated at 15° C. for 3 hours, followed by addition of 120 μl of sterile water to give a total volume of 150 μl.

(2) Transformation of E. coli with the plasmid

To 150 μl of the plasmid DNA (approximately 0.5 μl in weight) obtained by the procedure (1) were added an equal volume of competent cells of E. coli and the resultant preparation was allowed to stand at 0° C. for 10 minutes. The cells of E. coli were grown in 0.7 ml of L-broth at 37° C. for an hour. The culture was plated onto the surface of an agar plate which consisted of L-broth containing 1.5% agar and 20 μg/ml tetracycline and the cells were further grown overnight at 37° C. Four transformants which formed colonies on the agar plate were checked for the sizes of the plasmid retained by each of the clones.

(3) Extraction and determination of molecular weight of plasmid and confirmation of recognition and cleavage site for EcoRI.

Each of the transformants obtained by the procedure (2) above was suspended in 0.2 ml of a solution consisting of 0.2 mg/ml lysozyme and 0.05 mg/ml ribonuclease (RNase). The resultant preparation, with addition of 0.2 ml of 0.2% dodecylsodiumsulfate (SDS) solution, was incubated at room temperature for 1 to 2 minutes, subsequently allowed to stand at 0° C. for 10 minutes, and centrifuged at 20,000 rpm for 10 minutes at 0° C. To the supernatant thus obtained was added an equal volume of phenol saturated with buffer "A" which consisted of 10 mM Tris and 0.1 mM EDTA (pH 7.4), followed by vigorous shaking. The resultant mixture was centrifuged at 15,000 rpm for 3 minutes at room temperature to collect the aqueous layer containing DNA. Fifteen microliter fractions of the DNA-containing preparation were electrophoresed on a 0.8% agarose gel. Molecular weight of the DNA extracted from each of the four transformants was about 3.4 Md.

Tests were then conducted to make certain that the lefthand one (FIG. 15) of its two EcoRI sites in the original plasmid is absent in the DNA extracted from some of the four transformants as had been expected. For this purpose, the DNA extracted from the transformants was further collected by the previously described ethanol precipitation procedure, from the remaining fractions of the DNA-containing aqueous layer. The collected DNA (plasmid DNA) was dissolved in 100 μl of the buffer "A". To 10 μl of the resultant solution of the plasmid DNA were added 10 μl of a 2-fold concentrated buffer (containing 20 mM Tris-HCl (pH 7.6), 14 mM MgCl$_2$, 14 mM β-mercaptoethanol and 100 mM NaCl) and 2 μl of 6 unit/μl EcoRI. The mixture was incubated at 37° C. for 60 minutes and was heated at 70° C. for 5 minutes to terminate the reaction. The total reaction mixture was electrophoresed on a 0.8% agarose gel, with the result that two groups of the DNA fragments produced by cleaving each plasmid (pHY340) at one of the EcoRI sites were collected. To 10 μl each of these two groups of DNA fragments were added 10 μl of a 2 fold concentrated buffer (containing 20 mM Tris-HCl (pH 7.6), 14 mM MgCl$_2$, 14 mM β-mercaptoethanol and 100 mM NaCl) and 2 μl each of 5 unit/μl SacII and 6 unit/μl EcoRI. The mixture was incubated at 37° C. for 60 minutes. The reaction was terminated at 70° C. in 5 minutes thereafter and the total reaction mixture was electrophoresed on a 0.8% agarose gel, with the result that a group of the plasmids which had been cut at the righthand one of its EcoRI sites were collected as had been expected. This particular plasmid was named plasmid pHY339 (FIG. 15).

(4) Insertion of HindII linker

To 30 μl of the plasmid DNA pHY339 (approximately 0.1 μg/ml were added 5 μl of a 10-fold concentrated buffer (containing 100 mM Tris-HCl (pH 7.6), 70 mM MgCl$_2$, 7 mM β-mercaptoethanol and 500 mM NaCl), and 5 μl of 8 unit/μl SacII. The mixture was incubated at 37° C. for 60 minutes to digest the DNA molecules with the restriction enzyme SacII and was heated at 70° C. for 5 minutes to terminate the reaction and was thereafter electrophoresed on a 1% low-melting-point agarose slab gel (containing 1 μg/ml of ethydium bromide) similar to that used in the procedure (1). The plasmid DNA fragments of the molecular weight of 3.4 Md which were cut at the SacII site were extracted from the gel plate and the DNA fragments thus extracted were collected therefrom by phenol treatment and the cold ethanol precipitation procedure. The DNA fragments were dissolved in 20 μl of buffer "A". A 5 μl fraction of the resultant DNA solution was electrophoresed on a 0.8% agarose gel with the result that each of the plasmid DNA fragments was found to have the molecular weight of about 3.4 Md. The 15 μl fraction of the resultant DNA solution was treated with T4 DNA polymerase following the steps used in the procedure (1), whereupon DNA fragments were collected also by performing phenol treatment and the cold ethanol precipitation procedure. The collected DNA fragments were dissolved in 20 μl of buffer "A". To the resultant solution was added 1 μl of phosphorylated HindIII linker (dpCAAGCTTG; available from Takara Shuzo Co., Ltd., Japan; 0.01 optical density/ml). The resultant preparation was treated with T4 DNA ligase as in the procedure (1) to insert the linker to each of the DNA fragments and to circularize the DNA fragments. The solution was diluted with 120 μl of sterile water to give a total volume of 150 μl.

(5) Transformation of E. coli with the plasmid

Following the steps of the procedure (2), transformation of *E. coli* was carried out with use of the 150 μl of DNA solution (approximately 1 μl) obtained as a result of the procedure (4).

(6) Extraction and determination of molecular weight of plasmid and confirmation of recognition and cleavage site for HindIII.

Following steps of the procedure (3) but using the transformants obtained by the procedure (5), the plasmid DNAs were extracted from several of the transformants for the estimations of their molecular weight. The result revealed that the DNA molecule at each plasmid had the molecular weight of about 3.4 megadaltons.

Tests were further conducted to make certain that the DNA molecule of each plasmid extracted from the transformants contains the HindIII site. For this purpose, 20 μl of the plasmid DNA thus extracted was added with 2 μl of a 10-fold concentrated buffer containing 100 mM Tris-HCl (pH 7.6), 70 mM MgCl$_2$, 70 mM β-mercaptoethanol and 500 mM NaCl, and 3 μl of 10 unit/μl HindIII. The mixture was incubated at 37° C. for 90 minutes and was then heated at 70° C. for 5 minutes to terminate the reaction. The total reaction mixture was electrophoresed on a 0.8% agarose gel, with the result that the original plasmid DNA was found to be able to be cut at the HindIII site. This particular plasmid was named pHY336.

(7) Insertion of polylinker (i) Preparation of the polylinker

Plasmid πAN7 (a gift from Professor Saito's Office, Institute of Applied Microbiology, the University of Tokyo) was employed to prepare a polylinker having recognition and cleavage sites for the restriction enzymes in the sequence of $$\text{Eco}RI - \begin{pmatrix} \text{Sma}I \\ \text{Xma}I \end{pmatrix} - \text{Bam}HI - \begin{pmatrix} \text{Sal}I \\ \text{Acc}I \\ \text{Hinc}II \end{pmatrix} - \text{Pst}I -$$

$$\text{Bgl}II - \text{Xba}I - \text{Hind}III.$$

To 20 μl of the plasmid πAN7 (2 mg/ml) were added 3 μl of a 10-fold concentrated buffer (containing 100 mM Tris-HCl (pH 7.6), 70 mM MgCl$_2$, 70 mM β-mercaptoethanol and 500 mM NaCl), 5 μl of sterile water, and 3 μl of 10 unit/μl HindIII. The mixture was incubated at 37° C. for 60 minutes to digest the plasmid with HindIII. Thereafter, 3 μl of 6 unit/μl EcoRI was added to the reaction mixture, followed by further incubation at 37° C. for 60 minutes to further digest the plasmid with EcoRI. For the purpose of disintegrating into pieces each of the DNA fragments outside the polylinker region, 2 μl of 3.5 unit/μl HaeIII was added to the reaction mixture. The resultant preparation was incubated at 37° C. for 60 minutes and the reaction was terminated at 70° C. in 5 minutes thereafter. The reaction mixture was subjected to phenol treatment and ethanol precipitation procedure to collect the precipitates of DNA fragments following some of the steps of the procedure (1).

(ii) Preparation of vector.

To 30 μl of plasmid pHY336 (approximately 0.1 μg/μl) were added 3.5 μl of a 10-fold concentrated buffer containing 100 mM Tris-HCl (pH 7.6), 70 mM MgCl$_2$, 70 mM β-mercaptoethanol and 500 mM NaCl, and 3 μl of 10 unit/μl HindIII. the mixture was incubated at 37° C. for 60 minutes. To the reaction mixture, 3 μl of 6 unit/μl EcoRI was added and further incubated at 37° C. for 60 minutes and the reaction was terminated at 70° C. in 5 minutes thereafter. The resultant reaction mixture was electrophoresed on a 0.8% agarose gel, with the result that the plasmid DNA fragments were found to have breaks at their HindIII and EcoRI sites. The DNA fragments were recovered by performing phenol treatment and an ethanol precipitation procedure also following some of the steps of procedure (1).

(iii) Insertion of polylinker into vector.

Each of the polylinker obtained by the steps (i) and the vector prepared by the steps (ii) above dissolved in 10 μl of sterile water. The two solutions were then mixed together and thereafter the resultant solution was subjected to the ligation step of the procedure (1) to insert the polylinker into the vector, followed by addition of sterile water to give a total volume of 150 μl.

(8) Transformation of *E. coli* with the plasmid

Following the steps of the procedure (2), transformation of *E. coli* was carried out with use of the polylinker-carrying DNA molecules (approximately 1 μl) obtained by the steps (iii) of the procedure (7) above. The sizes of the plasmid DNA molecules carried on the transformants thus obtained were then determined.

(9) Extraction and determination of molecular weight of the plasmid and confirmation of the presence of polylinker.

Following the steps of the procedure (3) but using the transformants obtained by the procedure (8), molecular weight estimations were carried out on the plasmids extracted from 40 strains selected from the transformants. Out of these DNA plasmids, those which have revealed to have molecular weights of about 3.0 Md were further selected for treatment with phenol, thus collecting DNA molecules as in the procedure (1).

These plasmids were then cleaved at their cleavage sites for the restriction enzymes EcoRI, SmaI, BamHI, SalI, PstI, BglII, XbaI and HindIII to see if the polylinker derived from the plasmid πAN7 had actually been inserted into each of the plasmids. For this purpose, the plasmid DNA obtained from the transformants were dissolved in 100 μl of buffer "A". The resultant preparation was divided into eight 10 μl fractions, to each of which were further added 10 μl of a 2-fold concentrated buffer containing 20 mM Tris-HCl (pH 7.6), 14 mM MgCl₂, 14 mM β-mercaptoethanol and 100 mM NaCl, and thereafter 1 μl of 6 unit/μl EcoRI, 4 unit/μl SmaI, 1 unit/μl BamHI, 8 unit/μl SalI, 5 unit/μl PstI, 4.5 unit/μl BglII, 9 unit/ul XbaI, or 10 unit/μl HindIII. Each mixture was incubated at 37° C. for 60 minutes. The reaction was terminated at 70° C. in 5 minutes thereafter and the entire volume of each mixture was electrophoresed on a 0.8% agarose gel. It was found that all of the plasmid DNA contained in each mixture had breaks at the sites for EcoRI, SmaI, BamHI, SalI, PstI, BglII, XbaI and HindIII, showing that the plasmid pHY336 carried an insert of the polylinker. The polylinker-carrying plasmid thus obtained was named pHY300PLK.

(10) Transformation of E. coli and B. subtilis with plasmid pHY300PLK

To ascertain that the plasmid pHY300PLK is operable as a shuttle vector, transformation of E. coli and B. subtilis was performed with the DNA molecules extracted from the transformants used in the procedure (9) above. For reference purposes, plasmid pHY340 and plasmid pHY460 were used as control vectors, the latter being disclosed above.

(i) Transformation of E. coli

One hundred μl of competent cells of E. coli were added to 5 μl each of the plasmid DNA (approximately 1 μg) obtained in the course of the procedure (9), the plasmid pHY340 (approximately 1 μg) and the plasmid pHY460 (approximately 1 μg). Each resultant preparation was allowed to stand at 0° C. for 15 minutes to enable the DNA to penetrate into the cells of E. coli. The cells of E. coli were poured with 0.9 ml of L-broth and was then grown at 37° C. for an hour therein. Each culture thus obtained was plated onto an L-broth agar containing 1.5% agar and 20 μg/ml tetracycline and the cells were further grown overnight at 37° C.

(ii) Transformation of B. subtilis

Five hundred 10 μl of competent cells of B. subtilis were added to 10 μl each of the plasmid (approximately 1 μg) obtained in the course of the procedure (9), the plasmid pHY340 (approximately 1 μg) and the plasmid pHY460 (approximately 1 μg). The resultant preparations were cultured with shaking at 37° C. for 90 minutes. The cultured preparation was plated onto the surface of an agar plate similar to the medium used in the steps (i) above and the cells were further grown overnight at 37° C.

The numbers of the cells of E. coli and B. subtilis thus transformed per 1 μg each of the plasmids pHY300PLK, pHY340 and pHY460, and the ratio between such numbers are shown in the following table.

| Plasmid | pHY300PLK | pHY340 | pHY460 |
|---|---|---|---|
| E. coli | $8.3 \times 10^5$ | $9.5 \times 10^5$ | $8.3 \times 10^5$ |
| B. subtilis | $3.2 \times 10^5$ | $8.8 \times 10^4$ | $7.25 \times 10^4$ |
| B. subtilis/E. coli | 0.386 | 0.092 | 0.087 |

Figure 16:
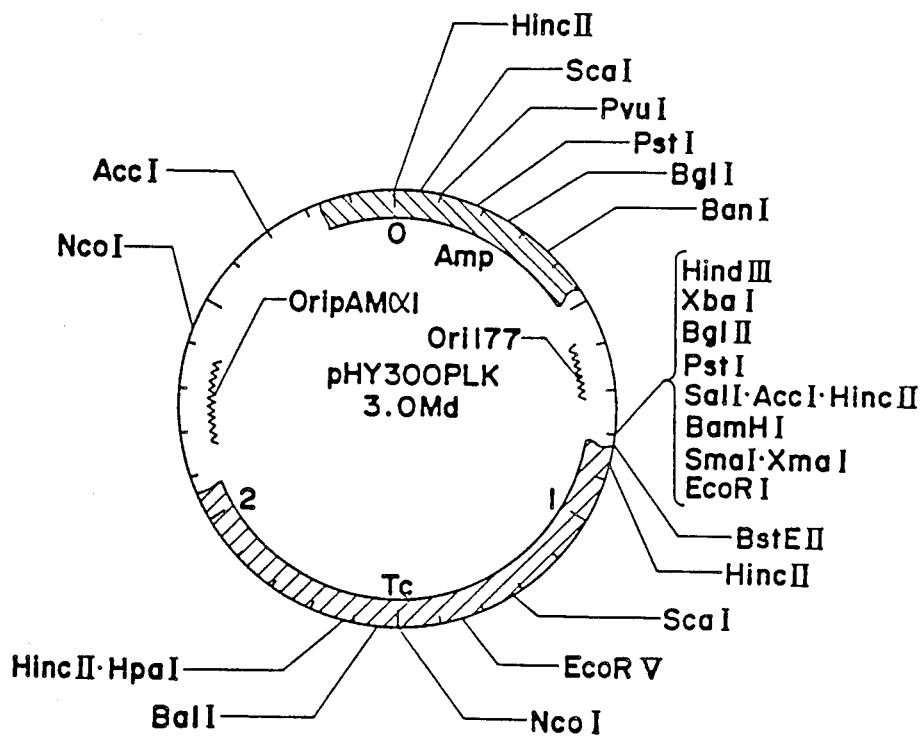
FIG. 16 is a cleavage map showing the sequence of the recognition and cleavage sites of the chimeric plasmid vector pHY300PLK.

The results shown in the table above demonstrate that the plasmid obtained in the course of the procedure (9) is a shuttle vector which reciprocates between E. coli and B. subtilis. This chimeric plasmid vector was named pHY300PLK, the cleavage map of which is shown in FIG. 16. The E. coli and B. subtilis transformed with this plasmid pHY300PLK have been deposited under the names of Escherichia coli C600 (pHY300PLK) and Bucillus subtilis (pHY300PLK) at Fermentation Research Institute, Agency of Industrial Science and Technology of Japan, as Deposition No. FERM BP-744 and FERM BP-753, respectively.

EXAMPLE 2

Figure 17:
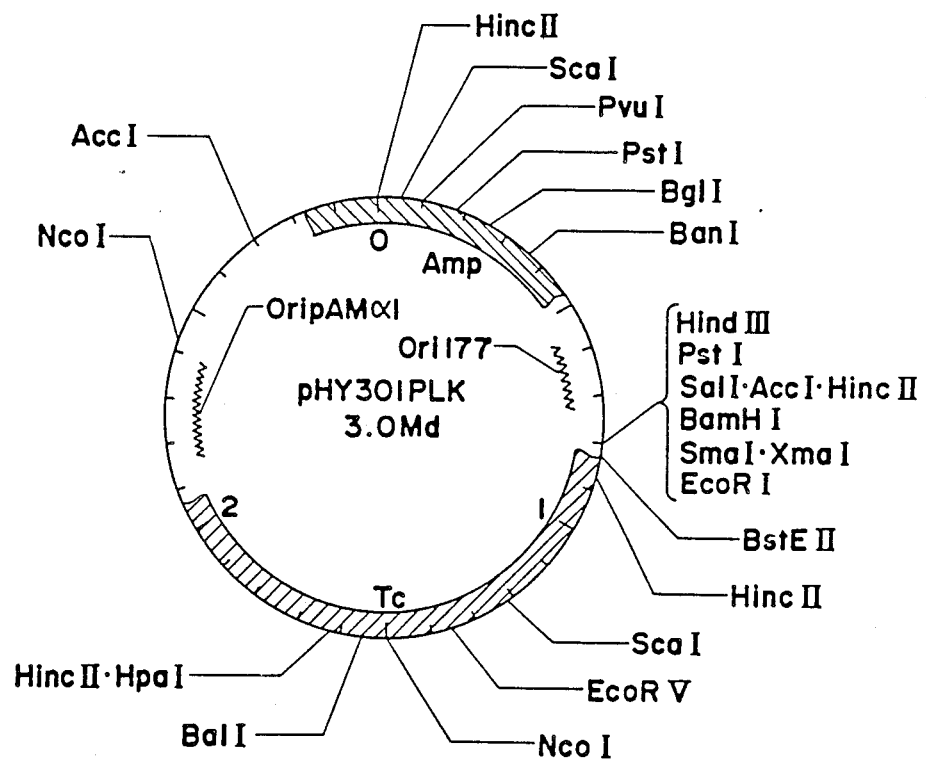
FIG. 17 is a cleavage map showing the sequence of the recognition and cleavage sites of another preferred example, named pHY301PLK, of a chimeric plasmid vector according to the present invention.

Plasmid pHY301PLK was prepared, following the procedures of Example 1 with the exception that a polylinker (commercially available from Amersham (UK), Code No. M13mp8) having a sequence of recognition and cleavage sites, as shown in FIG. 17, for the following series of restriction enzymes:

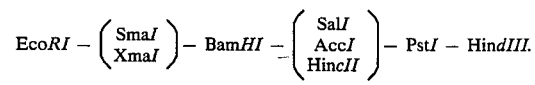

It was ascertained that the plasmid pHY301PLK was also operable as a shuttle vector between E. coli and B. subtilis.

EXAMPLE 3

Figure 18:
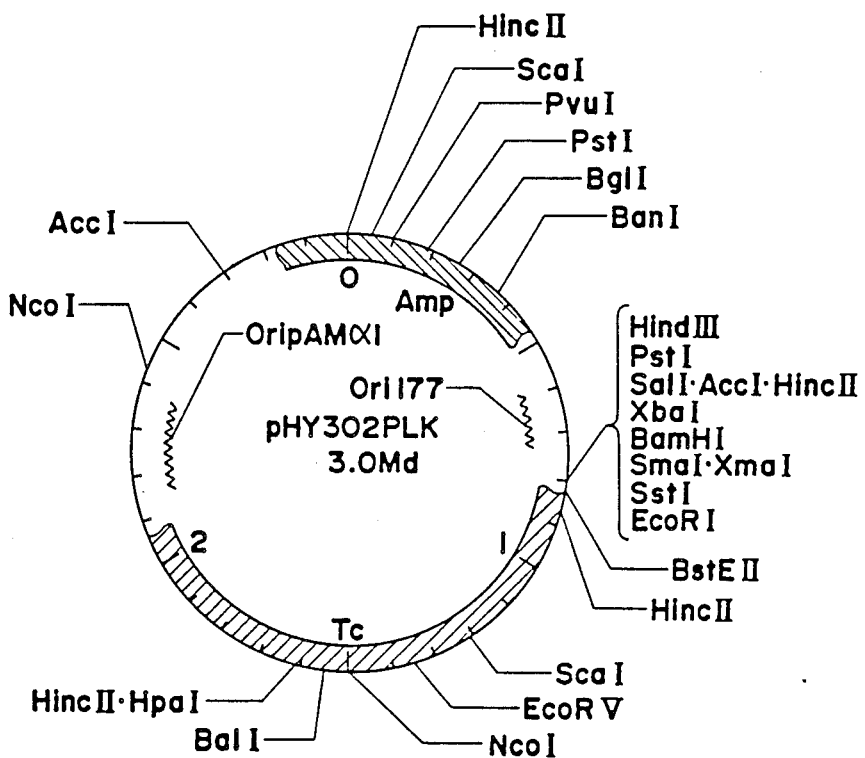
FIG. 18 is a cleavage map showing the sequence of the recognition and cleavage sites of still another example, named pHY302PLK, of a chimeric plasmid vector according to the present invention.

Plasmid pHY302PLK was prepared, following the procedures of Example 1 with the exception that a polylinker (commercially available from Amersham, Code No. M13mp10) having a sequence of recognition and cleavage sites, as shown in FIG. 18, for the following series of restriction enzymes:

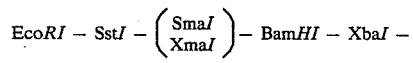

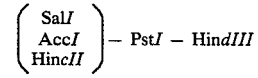

It was also ascertained that the plasmid pHY302PLK was operable as a shuttle vector between E. coli and B. subtilis.

Albeit the present invention has been described with reference to specific chimeric plasmids, pHY780, pHY600, pHY460, pHY385, pHY360, pHY340, pHY330, pHY310, pHY285, pHY225, pHY300PLK, pHY301PLK and pHY302PLK, this description is not meant to be construed in a limiting sense.

Various modifications of the described embodiments, as well as other embodiments of this invention, will become apparent to persons skilled in the art upon reference to the description of the present invention. It is therefore contemplated that the appended claims will cover any such modifications or embodiments as fall within the true scope of this invention.

Figure 7:
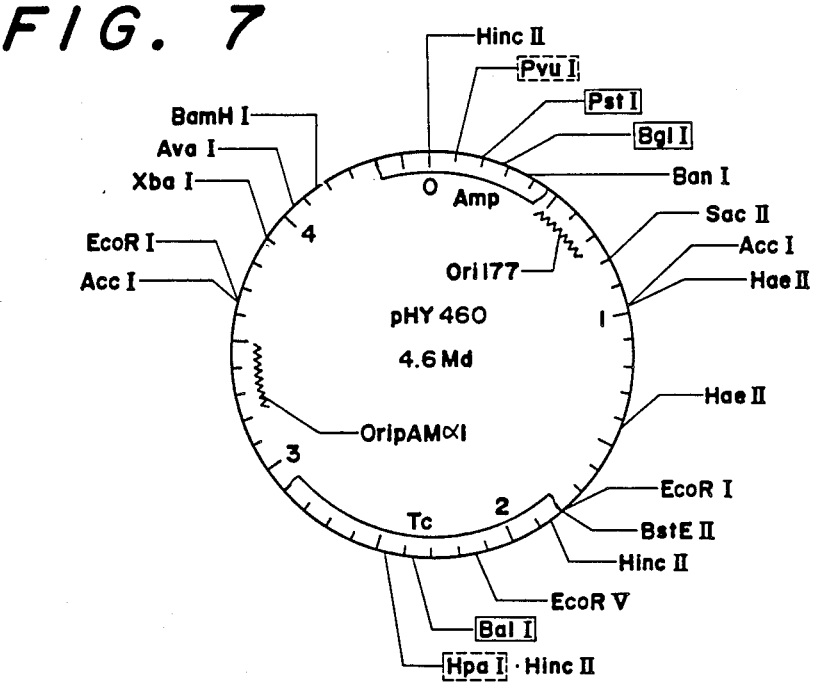
FIG. 7 is a cleavage map showing the sequence of the recognition and cleavage of chimeric plasmid pHY460 of the present invention.

What is claimed is:

1. A chimeric plasmid denoted pHY460 comprising:
   (a) a tetracycline resistance gene of plasmid pAMα1 and a first DNA replication origin of plasmid pAMα1, said tetracycline resistance gene being operable as a marker gene in strains of both *Escherichia coli* and *Bacillus subtillis* and said first DNA replication origin being operable in strains of *Bacillus subtillis;*
   (b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli;*
   (c) a unique restriction and cleavage site for the restriction enzyme BalI within said tetracycline resistance gene;
   (d) a unique restriction and cleavage site for the restriction n enzyme BglI within said ampicillin resistance gene; and
   (e) a unique restriction and cleavage site for the restriction enzyme PstI within said ampicillin resistance gene,
   wherein the approximate molecular weight of said chimeric plasmid is 4.6 Md and the cleavage map of the plasmid is as shown is FIG. 7 of the Drawings.

Figure 8:
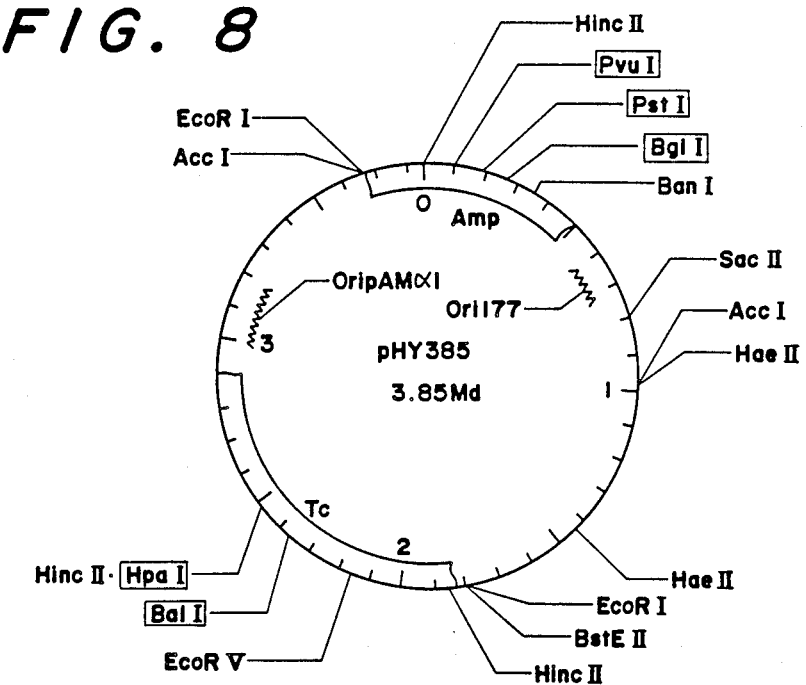
FIG. 8 is a cleavage map showing the sequence of the recognition and cleavage of chimeric plasmid pHY385 of the present invention.
Figure 9:
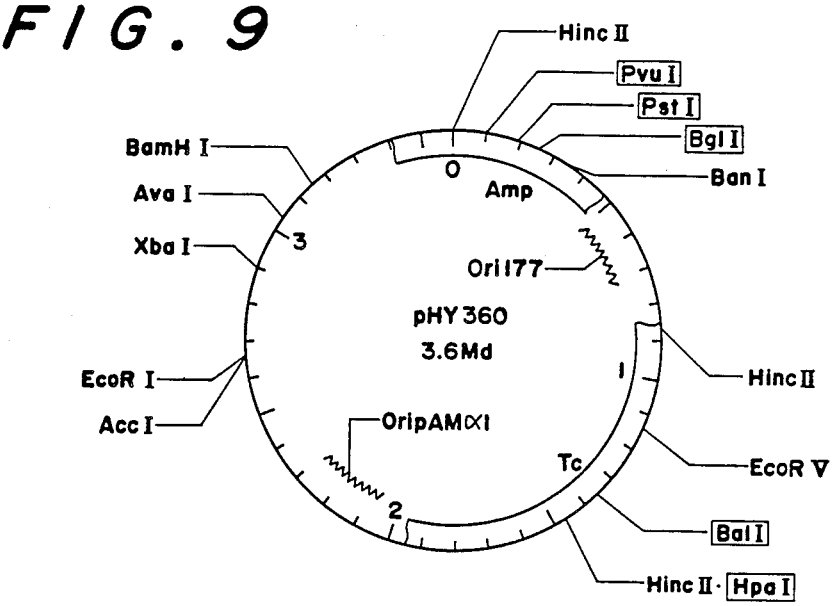
FIG. 9 is a cleavage map showing the sequence of the recognition and cleavage of chimeric plasmid pHY360 of the present invention.

2. A chimeric plasmid denoted pHY385 comprising:
   (a) a tetracycline resistance gene and a first DNA replication origin, both separated from a plasmid pAMα1, said tetracycline resistance gene being operable as a marker gene in strains of both *Escherichia coli* and *Bacillus subtilis* and said first DNA replication origin being operable in strains of *Bacillus subtilis;*
   (b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli;*
   (c) a unique restriction and cleavage site for the restriction enzyme BalI within said tetracycline resistance gene;
   (d) a unique restriction and cleavage site for the restriction enzyme BglI within said ampicillin resistance gene; and
   (e) a unique restriction and cleavage site for the restriction enzyme PstI within said ampicillin resistance gene,
   wherein the approximate molecular weight of said chimeric plasmid is 3.85 Md and the cleavage map of the plasmid is as shown in FIG. 8 of the Drawings.

Figure 10:
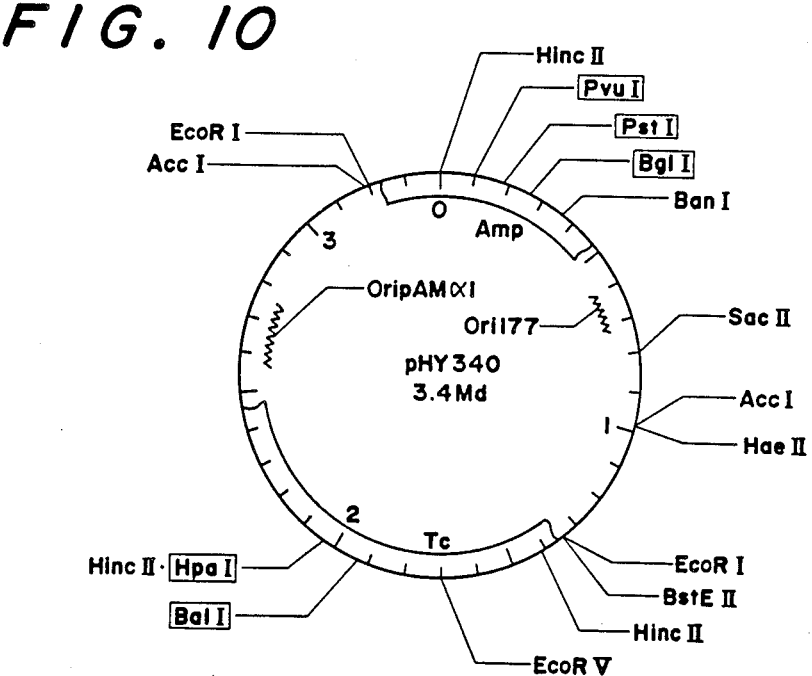
FIG. 10 is a cleavage map showing the sequence of the recognition and cleavage of chimeric plasmid pHY340 of the present invention.
Figure 11:
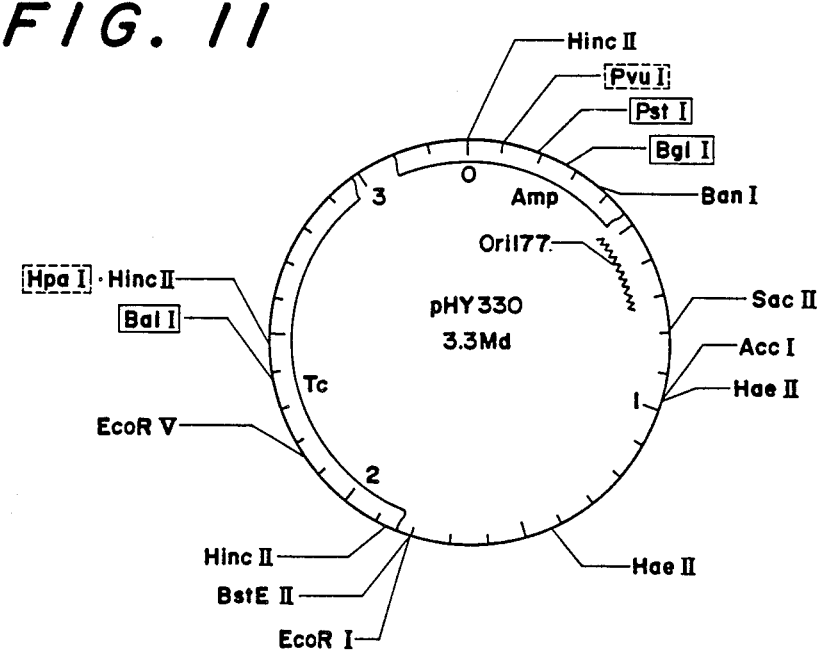
FIG. 11 is a cleavage map showing the sequence of the recognition and cleavage of chimeric plasmid pHY330 of the present invention.
Figure 12:
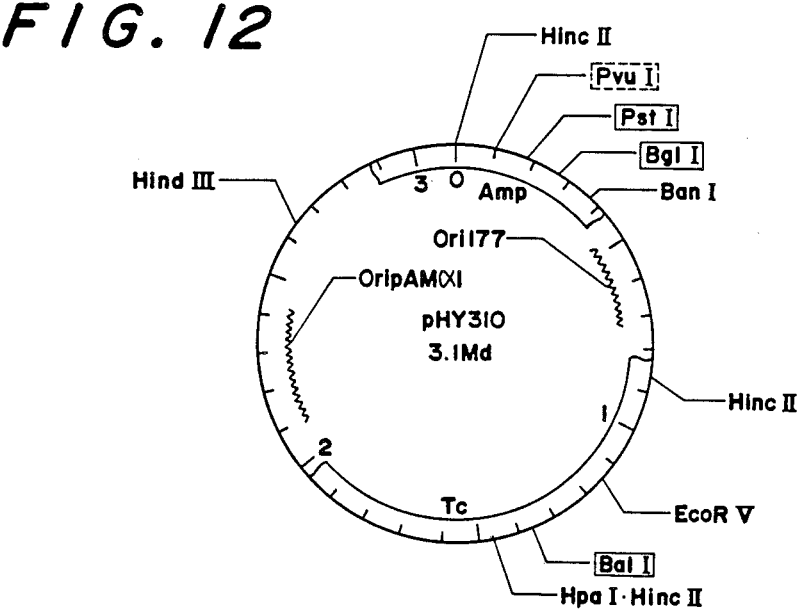
FIG. 12 is a cleavage map showing the sequence of the recognition and cleavage of chimeric plasmid pHY310 of the present invention.
Figure 13:
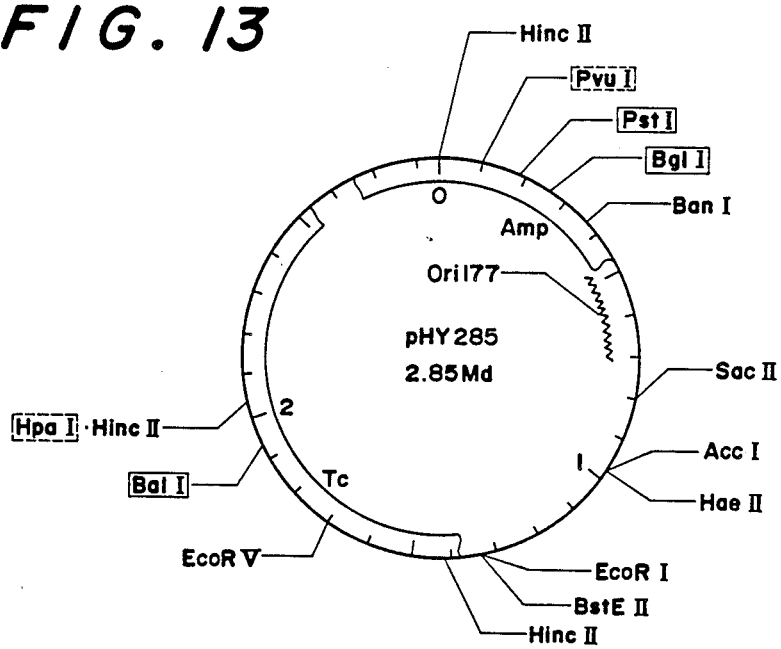
FIG. 13 is a cleavage map showing the sequence of the recognition and cleavage of chimeric plasmid pHY285 of the present invention.
Figure 14:
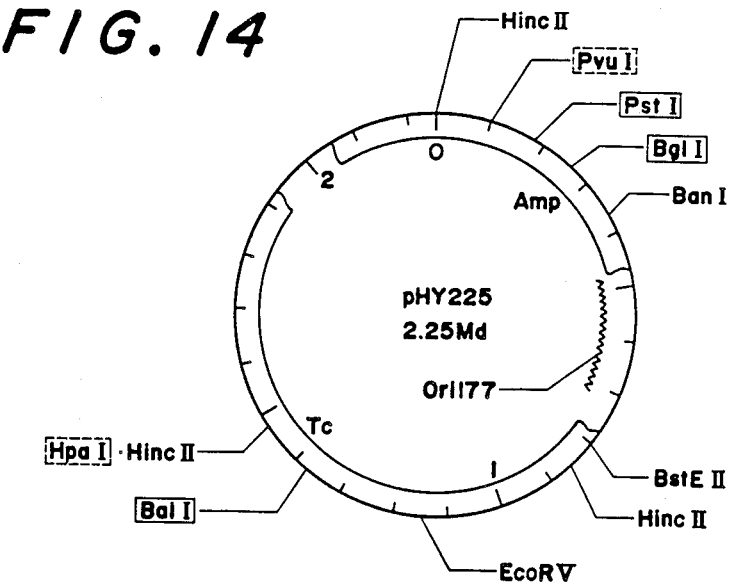
FIG. 14 is a cleavage map showing the sequence of the recognition and cleavage of chimeric plasmid pHY225 of the present invention.

3. A chimeric plasmid denoted pHY340 comprising:
   (a) a tetracycline resistance gene and a first DNA replication origin, both separated from a plasmid pAMα1, said tetracycline resistance gene being operable as a marker gene in strains of both *Escherichia coli* and *Bacillus subtilis* and said first DNA replication origin being operable in strains of *Bacillus subtilis;*
   (b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli;*
   (c) a unique restriction and cleavage site for the restriction enzyme BalI within said tetracycline resistance gene;
   (d) a unique restriction and cleavage site for the restriction enzyme BglI within said ampicillin resistance gene; and
   (e) a unique restriction and cleavage site for the restriction enzyme PstI within said ampicillin resistance gene,
   wherein the approximate molecular weight of said chimeric plasmid is 3.4 Md and the cleavage map of the plasmid is as shown in FIG. 10 of the Drawings.

4. A chimeric plasmid denoted pHY300PLK comprising:
   (a) a tetracycline resistance gene and a first DNA replication origin, both separated from a plasmid pAM-alphal, said tetracycline resistance gene being operable as a marker gene in strains of both *Escherichia coli* and *Bacillus subtilis* and said first DNA replication origin being operable in strains of *Bacillus sutilis;*
   (b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli;*
   (c) the unique restriction and cleavage sites for the respective restriction enzymes BstEII, EcoRV, BalI and HpaI within said tetracycline resistance gene;
   (d) the unique restriction and cleavage sites for the respective restriction enzymes PvuI, BglI and BanI within said ampicillin resistance gene;
   (e) a polylinker region composed of a DNA fragment having a recognition and cleavage site for the restriction enzyme EcoRI at one terminal and a recognition and cleavage site for the restriction enzyme HindIII at the other terminal thereof and having a nucleotide sequence of 5'-GAATTCCCGGGGATCCGTCGACCTGCAGATCTCTAGAAGCTT-3'
   (f) the unique restriction and cleavage sites for the respective restriction enzymes HindIII, XbaI, BglII, SalI, BamHI, SmaI and EcoRI within said polylinker region, wherein the approximate molecular weight of said chimeric plasmid is 3.0 Md and the cleavage map of the plasmid is as shown in FIG. 16 of the Drawings.

5. A chimeric plasmid denoted pHY301PLK comprising:
   (a) a tetracycline resistance gene and a first DNA replication origin, both separated from a plasmid pAM-alphal, said tetracycline resistance gene being operable as a marker gene in strains of both *Escherichia coli* and *Bacillus subtilis* and said first DNA replication origin being operable in strains of *Bacillus subtilis;*
   (b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli;*
   (c) the unique restriction and cleavage sites for the respective restriction enzymes BstEII, EcoRV, BalI and HpaI within said tetracycline resistance gene;

(d) the unique restriction and cleavage sites for the respective restriction enzymes PvuI, BglI and BanI within said ampicillin resistance gene;

(e) a polylinker region composed of a DNA fragment having a recognition and cleavage site for the restriction enzyme EcoRI at one terminal and a recognition and cleavage site for the restriction enzyme HindIII at the other terminal thereof and having a nucleotide sequence of 5'-GAATTCCGGGGATCCGTCGACCT-GCAGCCAAGCTT-3'

(f) the unique restriction and cleavage sites for the respective restriction enzymes HindIII, SalI, BamHI, SmaI and EcoRI within said polylinker region, wherein the approximate molecular weight of said chimeric plasmid is 3.0 Md and the cleavage map of the plasmid is as shown in FIG. 17 of the Drawings.

6. A chimeric plasmid denoted pHY302PLK comprising;

(a) a tetracycline resistance gene and a first DNA replication origin, both separated from a plasmid pAM-alphal, said tetracycline resistance gene being operable as a marker gene in strains of both *Escherichia coli* and *Bacillus subtilis* and said first DNA replication origin being operable in strains of *Bacillus subtilis*;

(b) an ampicillin resistance gene and a second DNA replication origin, both separated from a vector pACYC177, said ampicillin resistance gene being operable as a marker gene solely in strains of *Escherichia coli* and said second DNA replication origin being operable in strains of *Escherichia coli*;

(c) the unique restriction and cleavage sites for the respective restriction enzymes BstEII, EcoRV, BalI and HpaI within said tetracycline resistance gene;

(d) the unique restriction and cleavage sites for the respective restriction enzymes PvuI, BglI and BanI within said ampicillin resistance gene;

(e) a polylinker region composed of a DNA fragment having a recognition and cleavage site for the restriction enzyme EcoRI at one terminal and a recognition and cleavage site for the restriction enzyme HindIII at the other terminal thereof and having a nucliotide sequence of 5'-GAATT-CGAGCTCGCCCGGGGATCCTCTAGAGT-CGACCTGCAGCCCAAGCTT-3'

(f) the unique restriction and cleavage sites for the respective restriction enzymes HindIII, SalI, XbaI, BamHI, SmaI, SstI and EcoRI within said polylinker region, wherein the approximate molecular weight of said chimeric plasmid is 3.0 Md and the cleavage map of the plasmid is as shown in FIG. 18 of the Drawings.

* * * * *